United States Patent
LaTour et al.

(10) Patent No.: US 12,044,648 B2
(45) Date of Patent: Jul. 23, 2024

(54) ANALYTE SENSORS AND SENSING METHODS FEATURING LOW-POTENTIAL DETECTION

(71) Applicant: Abbott Diabetes Care Inc., Alameda, CA (US)

(72) Inventors: John V. LaTour, Daly City, CA (US); Jonathan D. McCanless, Oakland, CA (US); Stephen Oja, Alameda, CA (US); Tianmei Ouyang, Fremont, CA (US); Kevin Paul Wallis, Castro Valley, CA (US); Benjamin J. Feldman, Berkeley, CA (US); Udo Hoss, San Ramon, CA (US); Suyue Qian, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 347 days.

(21) Appl. No.: 17/132,360

(22) Filed: Dec. 23, 2020

(65) Prior Publication Data

US 2021/0190718 A1    Jun. 24, 2021

Related U.S. Application Data

(60) Provisional application No. 62/952,558, filed on Dec. 23, 2019.

(51) Int. Cl.
*G01N 27/327* (2006.01)

(52) U.S. Cl.
CPC ..... *G01N 27/3272* (2013.01); *G01N 27/3277* (2013.01)

(58) Field of Classification Search
None
See application file for complete search history.

(56) References Cited

U.S. PATENT DOCUMENTS

| | | | |
|---|---|---|---|
| 6,134,461 | A | 10/2000 | Say et al. |
| 6,605,200 | B1 | 8/2003 | Mao et al. |

(Continued)

FOREIGN PATENT DOCUMENTS

| | | |
|---|---|---|
| JP | 2010168369 A | 8/2010 |
| KR | 2019 0123169 A | 10/2019 |

(Continued)

OTHER PUBLICATIONS

Communication Relating to the Results of the Partial International Search for related application PCT/US2020/066826 mailed Apr. 19, 2021.

(Continued)

*Primary Examiner* — J. Christopher Ball
(74) *Attorney, Agent, or Firm* — Sterne, Kessler, Goldstein & Fox P.L.L.C.

(57) ABSTRACT

Analyte sensors responsive at low working electrode potentials may comprise an active area upon a surface of a working electrode, wherein the active area comprises a (Continued)

polymer, a redox mediator covalently bonded to the polymer, and at least one analyte-responsive enzyme covalently bonded to the polymer. A specific redox mediator responsive at low potential may have a structure of

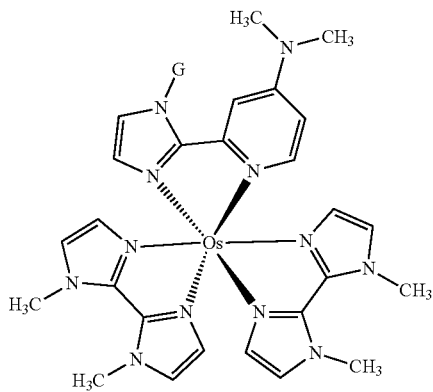

wherein G is a linking group covalently bonding the redox mediator to the polymer. A mass transport limiting membrane permeable to the analyte may overcoat the active area. In some sensor configurations, the mass transport limiting membrane may comprise a membrane polymer crosslinked with a branched crosslinker comprising three or more crosslinkable groups, such as polyethylene glycol tetraglycidyl ether.

12 Claims, 13 Drawing Sheets

(56) References Cited

U.S. PATENT DOCUMENTS

| | | |
|---|---|---|
| 6,605,201 B1 | 8/2003 | Mao et al. |
| 6,736,957 B1 | 5/2004 | Forrow et al. |
| 7,501,053 B2 | 3/2009 | Karinka et al. |
| 7,754,093 B2 | 7/2010 | Forrow et al. |
| 8,268,143 B2 | 9/2012 | Liu et al. |
| 8,444,834 B2 | 5/2013 | Liu et al. |
| 2005/0084921 A1* | 4/2005 | Cranley .......... C12P 7/28 |
| | | 435/150 |
| 2011/0213225 A1 | 9/2011 | Bernstein et al. |
| 2012/0132525 A1 | 5/2012 | Liu |
| 2012/0138484 A1 | 6/2012 | Bommakanti |
| 2019/0320947 A1 | 10/2019 | Chen |
| 2021/0190719 A1 | 6/2021 | Latour et al. |

FOREIGN PATENT DOCUMENTS

| | | |
|---|---|---|
| WO | 2001/036430 A1 | 5/2001 |
| WO | WO-2008118257 A1 | 10/2008 |
| WO | 2010/030912 A1 | 3/2010 |
| WO | WO-2017151952 A1 * | 9/2017 ......... A61B 5/14865 |

OTHER PUBLICATIONS

International Search Report and Written Opinion for International Application No. PCT/US2020/066826, European Patent Office, Netherlands, mailed on Nov. 6, 2021.
LibreText webpage on "Reference Electrodes", access from https://chem.libretexts.org/@go/page/78002 on Jul. 27, 2023.
Office Action mailed Aug. 1, 2023, in U.S. Appl. No. 17/151,296, 12 pages.
Final Office Action mailed Nov. 30, 2023, in U.S. Appl. No. 17/151,296, 12 pages.

* cited by examiner

ANALYTE SENSORS AND SENSING METHODS FEATURING LOW-POTENTIAL DETECTION

BACKGROUND

The detection of various analytes within an individual can sometimes be vital for monitoring the condition of their health. Deviation from normal analyte levels can often be indicative of a number of physiological conditions. Glucose levels, for example, can be particularly important to detect and monitor in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Other analytes may be desirable to monitor for other physiological conditions. Monitoring of multiple analytes may also be desirable in some instances, particularly for comorbid conditions that result in simultaneous dysregulation of two or more analytes in combination with one another.

Many analytes represent intriguing targets for physiological analyses, provided that a suitable detection chemistry can be identified. To this end, amperometric sensors configured for assaying glucose continuously in vivo have been developed and refined over recent years to aid in monitoring the health of diabetic individuals. Other analytes commonly subject to concurrent dysregulation with glucose in diabetic individuals include, for example, lactate, oxygen, pH, A1c, ketones, and the like. It can also be desirable to monitor these and other analytes independent of glucose dysregulation as well. Analyte sensors configured for detecting analytes other than glucose in vivo are known but are considerably less refined at present. Poor sensitivity for low-abundance analytes may be especially problematic.

Analyte monitoring in an individual may take place periodically or continuously over a period of time. Periodic analyte monitoring may take place by withdrawing a sample of bodily fluid, such as blood or urine, at set time intervals and analyzing ex vivo. Periodic, ex vivo analyte monitoring can be sufficient to determine the physiological condition of many individuals. However, ex vivo analyte monitoring may be inconvenient or painful in some instances. Moreover, there is no way to recover lost data if an analyte measurement is not obtained at an appropriate time. Continuous analyte monitoring may be conducted using one or more sensors that remain at least partially implanted within a tissue of an individual, such as dermally, subcutaneously or intravenously, so that analyses may be conducted in vivo. Implanted sensors may collect analyte data on-demand, at a set schedule, or continuously, depending on an individual's particular health needs and/or previously measured analyte levels. Analyte monitoring with an in vivo implanted sensor may be a more desirable approach for individuals having severe analyte dysregulation and/or rapidly fluctuating analyte levels, although it can also be beneficial for other individuals as well. Since implanted analyte sensors often remain within a tissue of an individual for an extended period of time, it can be highly desirable for such analyte sensors to be made from stable materials exhibiting a high degree of biocompatibility.

To improve biocompatibility, analyte sensors may include a membrane disposed over the implanted portion of the sensor, particularly a membrane that overcoats at least the active area of the sensor. In addition to promoting biocompatibility, the membrane may be permeable or semi-permeable to an analyte of interest and limit the overall flux of the analyte to the active area of the sensor. Such mass transport limiting membranes may aid in avoiding overload (saturation) of the sensing components within the active area, thereby improving sensor performance and accuracy. For example, in the case of sensors employing enzyme-based detection, limiting mass transport of the analyte to the active area can make the chemical kinetics of the sensing process analyte-limited rather than enzyme-limited, thereby allowing the sensor output to be correlated readily with the amount of analyte present.

One issue associated with incorporating a membrane upon an analyte sensor is that the analyte flux across the membrane may vary considerably as a function of temperature and/or the length of time the analyte sensor has been implanted in a tissue. Some membrane materials are less prone to temperature-dependent analyte flux than are others. If needed, a calibration factor or equation may be employed to account for analyte flux variability as a function of temperature, although though doing so can add considerable complexity to use of the sensor. Compositional changes in a membrane may occur over time, particularly through extractive loss of various membrane components and/or through membrane degradation or metabolism, which may lead to differing analyte permeability values depending on the extent of compositional changes that has occurred. Compositional changes resulting in differing membrane permeability values may be difficult to address quantitatively, and it can sometimes be difficult to determine when the membrane permeability has stabilized sufficiently to allow for measurement of accurate analyte concentrations. Oftentimes, a several-hour or longer equilibration period may be employed when implanting a new analyte sensor in vivo to allow for stabilization of the analyte flux through the membrane.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
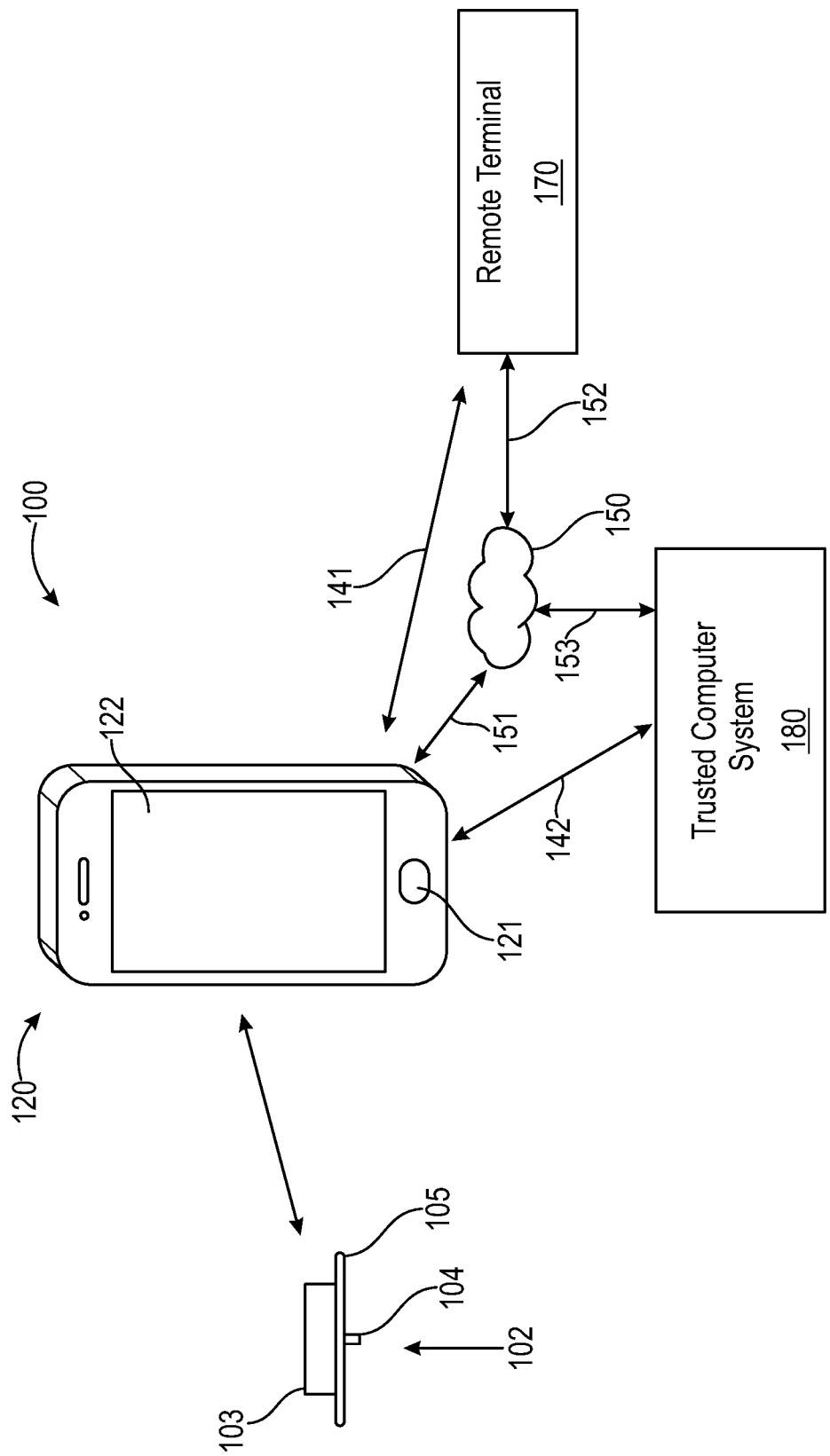
FIG. 1 shows a diagram of an illustrative sensing system that may incorporate an analyte sensor of the present disclosure.

The present disclosure generally describes analyte sensors suitable for in vivo use and, more specifically, analyte sensors comprising components that include features of low potential operation capability and/or stabilized membrane materials. Depending on sensor configuration, the analyte sensors of the present disclosure may be configured to detect one analyte or multiple analytes simultaneously or near simultaneously. Sequential dip coating operations to introduce differing membrane compositions upon the analyte sensors at specified locations may be performed.

Various analyte sensor components may cause certain difficulties during monitoring of some analytes or combinations of analytes. Redox mediators used to promote electron transfer to a working electrode may necessitate operation of an analyte sensor at relatively high potentials, which may lead to electrochemical side reactions that may complicate detection of some low-abundance analytes. Compositional changes in a mass transport limiting membrane within analyte sensors may lead to undesired analyte permeability variance while the analyte sensor is implanted in vivo, particularly during extended sensor wear. In addition, when analyzing for multiple analytes using a single analyte sensor, different analyte permeability properties may require utilization of dissimilar mass transport limiting membranes at various locations.

To address the foregoing needs, the present disclosure provides redox mediators for promoting electron transfer at lower working electrode potentials than are commonly used. Use of such "low-potential" redox mediators may lessen the occurrence of electrochemical side reactions by permitting analyte detection to take place at a lower potential than would otherwise be possible. By lessening the occurrence of electrochemical side reactions and signal noise associated therewith, detection of low-abundance analytes, such as ketones, may take place more readily than would otherwise be possible at higher working electrode potentials. Such low-potential redox mediators may also be advantageous when used in conjunction with detecting multiple analytes, as discussed further hereinbelow. Redox mediators capable of promoting analyte detection at low working electrode potentials are described further below.

Various crosslinked polyvinylimidazole and polyvinylpyridine membrane polymers may be used within analyte sensors to promote biocompatibility and to provide mass transport limiting properties. The functionalization upon the membrane material may be selected to modify analyte permeability and to limit the analyte permeability variance with temperature. Such membrane polymers may be crosslinked with a linear glycidyl ether having two crosslinkable groups, such as polyethylene glycol diglycidyl ether (PEGDGE), but there may still need to be an equilibration period following sensor implantation to allow the analyte flux to stabilize. Without being bound by theory or mechanism, it is believed that the membrane composition may change during the equilibration period as small amounts of extractable substances are liberated from the membrane, thereby potentially changing the analyte permeability. Surprisingly, the present disclosure shows that a branched crosslinker comprising three or more crosslinkable groups, such as a branched polyethylene glycol glycidyl ether, more specifically polyethylene glycol tetraglycidyl ether, may decrease the amount of extractable substances liberated from a membrane following sensor implantation. Decreased production of extractable substances from the membrane may be realized even when the crosslinking density and amount (mass) of crosslinker is otherwise substantially the same as that provided by a linear glycidyl ether having two crosslinkable groups. That is, a given mass of crosslinkable groups from a branched crosslinker, such as polyethylene glycol tetraglycidyl ether, may result in decreased extractables for a given membrane material compared that amount of extractables resulting from a substantially similar mass of crosslinkable groups from a linear glycidyl ether crosslinker, such as polyethylene glycol diglycidyl ether. Advantageously, decreased extractables may result from membrane materials crosslinked with a branched crosslinker, as disclosed herein, thereby affording an improved toxicological profile. In addition, the decreased compositional changes afforded by the membrane materials disclosed herein may afford shorter sensor equilibration times following sensor implantation, which may potentially extend the wear lifetime of the sensors.

Before describing the analyte sensors of the present disclosure and their components in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the communication paths or links, such as near field communication (NFC), radio frequency identification (RFID), BLU- ETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode. In certain configurations, the sensor tail may comprise a ketones-responsive active area, which may comprise a low-potential redox mediator in certain instances, as discussed further herein. A counter electrode may be present in combination with the at least one working electrode. Particular electrode configurations upon the sensor tail are described in more detail below.

One or more mass transport limiting membranes may overcoat the active area, as also described in further detail below, particularly a mass transport limiting membrane crosslinked with a branched glycidyl ether, such as polyethylene glycol tetraglycidyl ether. The active area may be configured for detecting a particular analyte. For example, a glucose-responsive active area may comprise a glucose-responsive enzyme, a lactate-responsive active area may comprise a lactate-responsive enzyme, and a ketones-responsive active area may comprise an enzyme system comprising at least two enzymes that are capable of acting in concert to facilitate detection of ketones. Suitable enzyme systems for detecting ketones are further described below in reference to FIGS. 6A-6C. Each active area may include a polymer to which at least some of the enzymes are covalently bonded, according to various embodiments.

In any embodiment of the present disclosure, one or more analytes may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine a concentration of one or more analytes in vivo.

Referring still to FIG. 1, sensor 104 may automatically forward data to reader device 120. For example, analyte concentration data (i.e., glucose and/or ketones concentrations) may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

Figure 2A:
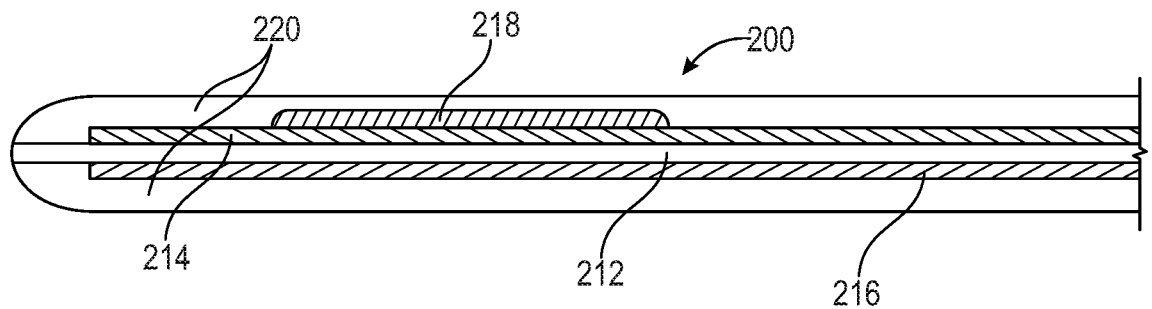
FIGS. 2A-2C show cross-sectional diagrams of analyte sensors comprising a single active area.
Figure 2B:
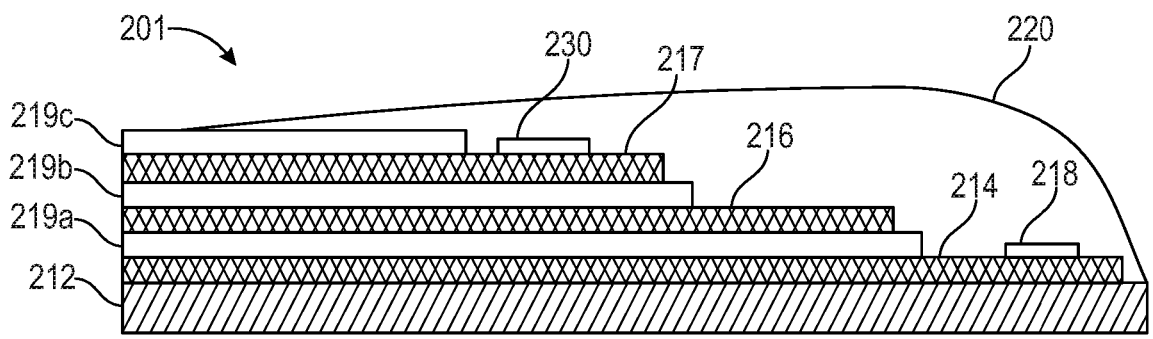
Figure 2C:
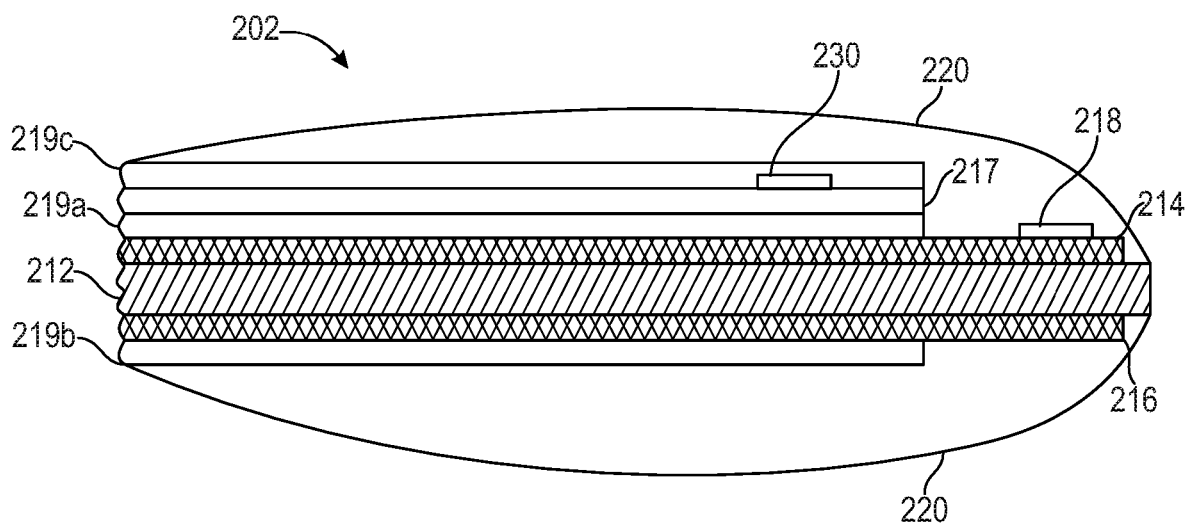

Sensor configurations featuring a single active area that is configured for detection of a corresponding single analyte may employ two-electrode or three-electrode detection motifs, as described further herein in reference to FIGS. 2A-2C. Sensor configurations featuring two different active areas for detection of separate analytes, either upon separate working electrodes or upon the same working electrode, are described separately thereafter in reference to FIGS. 3A-5C. Sensor configurations having multiple working electrodes may be particularly advantageous for incorporating two different active areas within the same sensor tail, since the signal contribution from each active area may be determined more readily. In addition, deposition of differing membrane compositions upon each active area may be readily conducted through sequential dip coating operations when the active areas are present on second working electrodes.

When a single working electrode is present in an analyte sensor, three-electrode sensor configurations may comprise a working electrode, a counter electrode, and a reference electrode. Related two-electrode sensor configurations may comprise a working electrode and a second electrode, in which the second electrode may function as both a counter electrode and a reference electrode (i.e., a counter/reference electrode). The various electrodes may be at least partially stacked (layered) upon one another and/or laterally spaced apart from one another upon the sensor tail. Suitable sensor configurations may be substantially flat in shape or substantially cylindrical in shape. In any of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

FIG. 2A shows a diagram of an illustrative two-electrode analyte sensor configuration, which is compatible for use in the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. Active area 218 may comprise multiple spots or a single spot configured for detection of an analyte at a low working electrode potential, as discussed further herein.

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 (i.e., membrane 220 is a mass transport limiting membrane having some permeability for the analyte of interest). According to the disclosure herein, membrane 220 may be crosslinked with a branched crosslinker in particular sensor configurations. The composition and thickness of membrane 220 may vary to promote a desired analyte flux to active area 218, thereby providing a desired signal intensity and stability. Analyte sensor 200 may be operable for assaying an analyte by any of coulometric, amperometric, voltammetric, or potentiometric electrochemical detection techniques.

FIGS. 2B and 2C show diagrams of illustrative three-electrode analyte sensor configurations, which are also compatible for use in the disclosure herein. Three-electrode analyte sensor configurations may be similar to that shown for analyte sensor 200 in FIG. 2A, except for the inclusion of additional electrode 217 in analyte sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219a, 219b and 219c separate electrodes 214, 216 and 217 from one another and provide electrical isolation. Alternately, at least one of electrodes 214, 216 and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 2A, active area 218 in analyte sensors 201 and 202 may comprise multiple spots or a single spot. Additionally, analyte sensors 201 and 202 may be operable for assaying an analyte by any of coulometric, amperometric, voltammetric, or potentiometric electrochemical detection techniques.

Like analyte sensor 200, membrane 220 may also overcoat active area 218, as well as other sensor components, in analyte sensors 201 and 202, thereby serving as a mass transport limiting membrane. Additional electrode 217 may be overcoated with membrane 220 in some embodiments. Although FIGS. 3B and 2C have depicted all of electrodes 214, 216 and 217 as being overcoated with membrane 220, it is to be recognized that only working electrode 214 may be overcoated in some embodiments. Moreover, the thickness of membrane 220 at each of electrodes 214, 216 and 217 may be the same or different and/or the membrane composition may vary locally. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

Figure 3A:
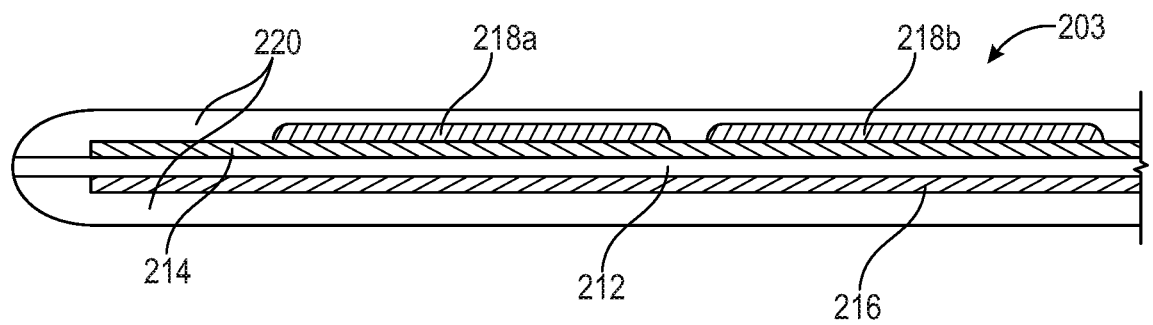
FIGS. 3A-4 show cross-sectional diagrams of analyte sensors comprising two active areas.

FIG. 3A shows an illustrative configuration for sensor 203 having a single working electrode with two different active areas disposed thereon. FIG. 3A is similar to FIG. 2A, except for the presence of two active areas upon working electrode 214: first active area 218a and second active area 218b, which are responsive to different analytes and are laterally spaced apart from one another upon the surface of working electrode 214. Active areas 218a and 218b may comprise multiple spots or a single spot configured for detection of each analyte. The composition of membrane 220 may vary or be compositionally the same at active areas 218a and 218b. First active area 218a and second active area 218b may be configured to detect their corresponding analytes at working electrode potentials that differ from one another, as discussed further below.

Figure 3B:
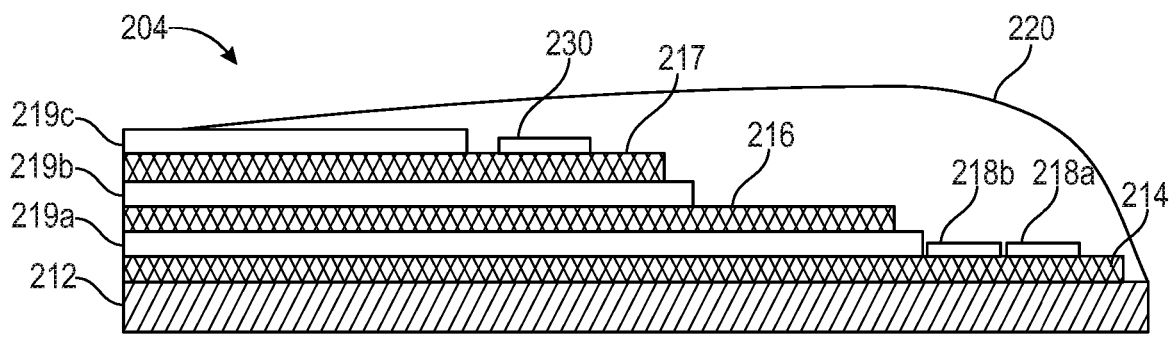
Figure 3C:
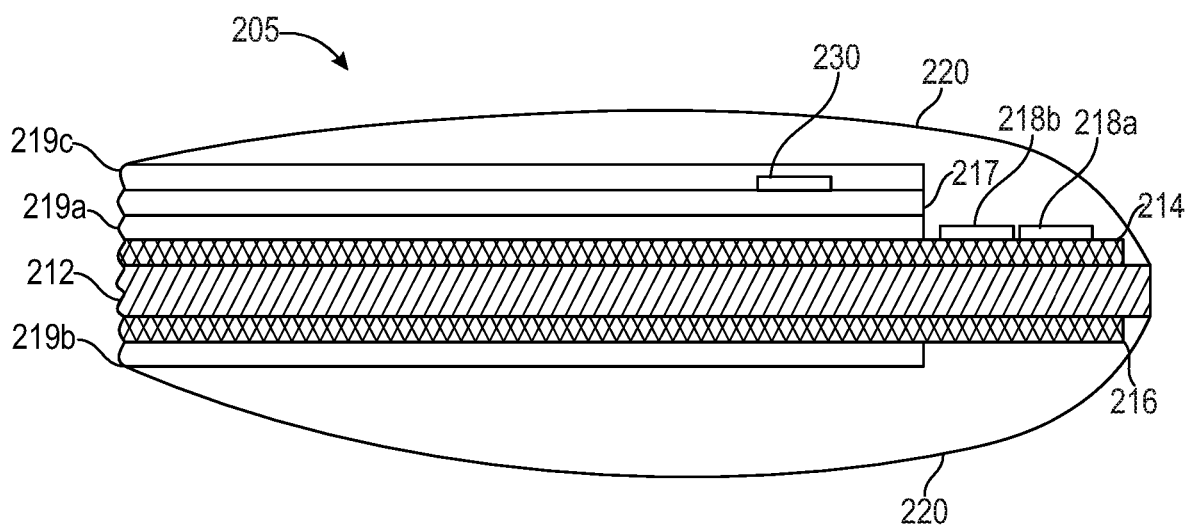

FIGS. 3B and 3C show cross-sectional diagrams of illustrative three-electrode sensor configurations for sensors 204 and 205, respectively, each featuring a single working electrode having first active area 218a and second active area 218b disposed thereon. FIGS. 3B and 3C are otherwise similar to FIGS. 2B and 2C and may be better understood by reference thereto. As with FIG. 3A, the composition of membrane 220 may vary or be compositionally the same at active areas 218a and 218b.

Figure 4:
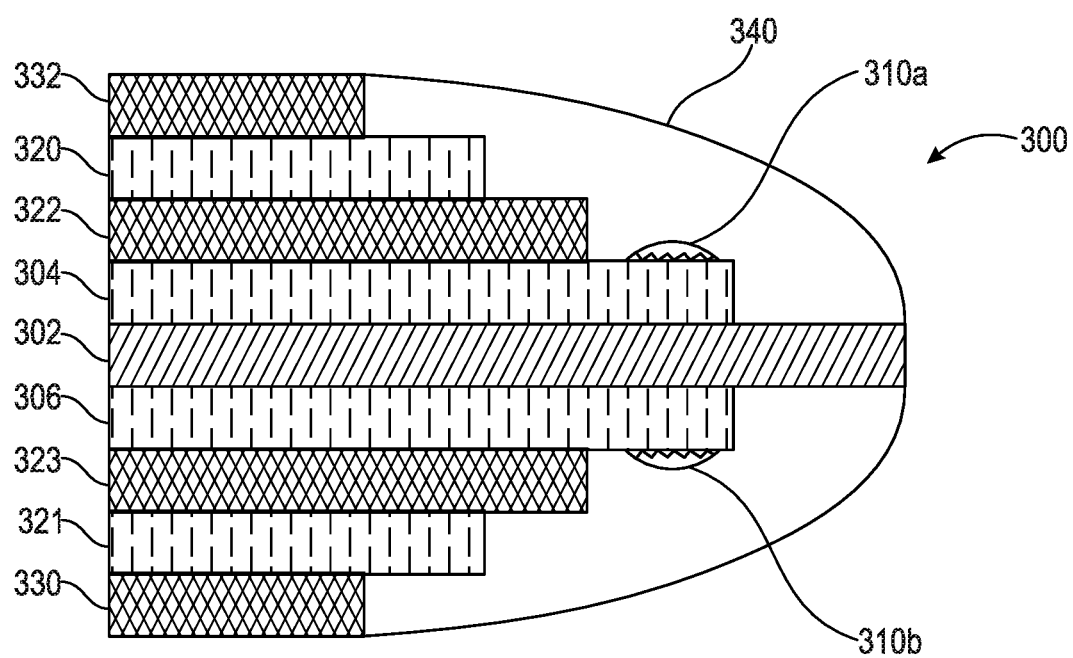
Figure 5A:
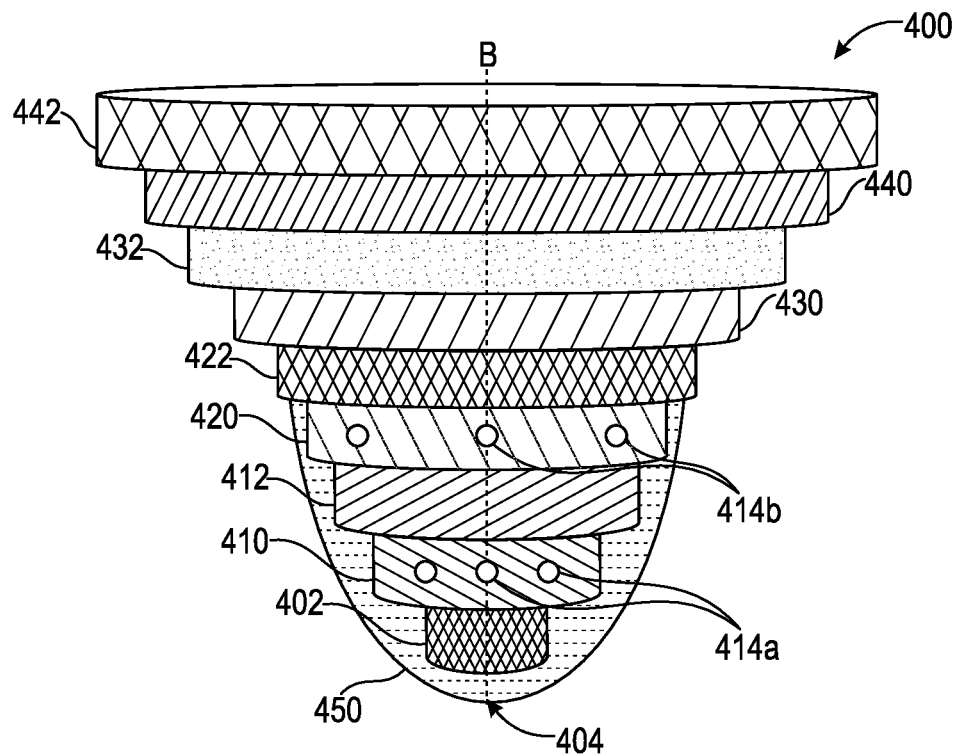
FIGS. 5A-5C show perspective view of analyte sensors comprising two active areas upon separate working electrodes.
Figure 5B:
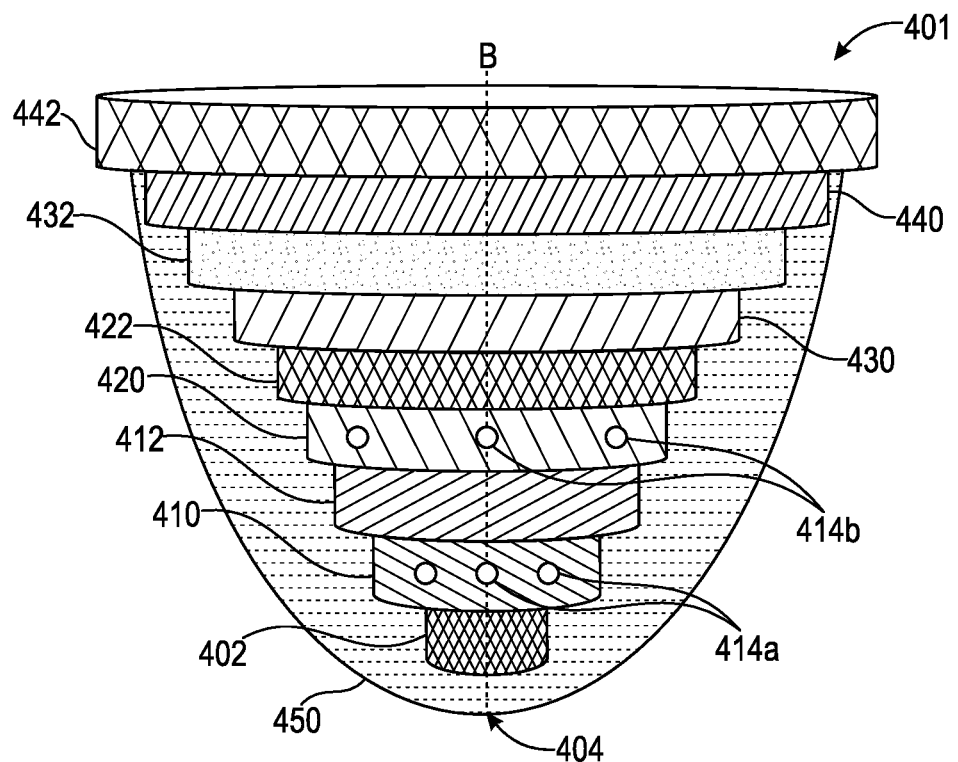
Figure 5C:
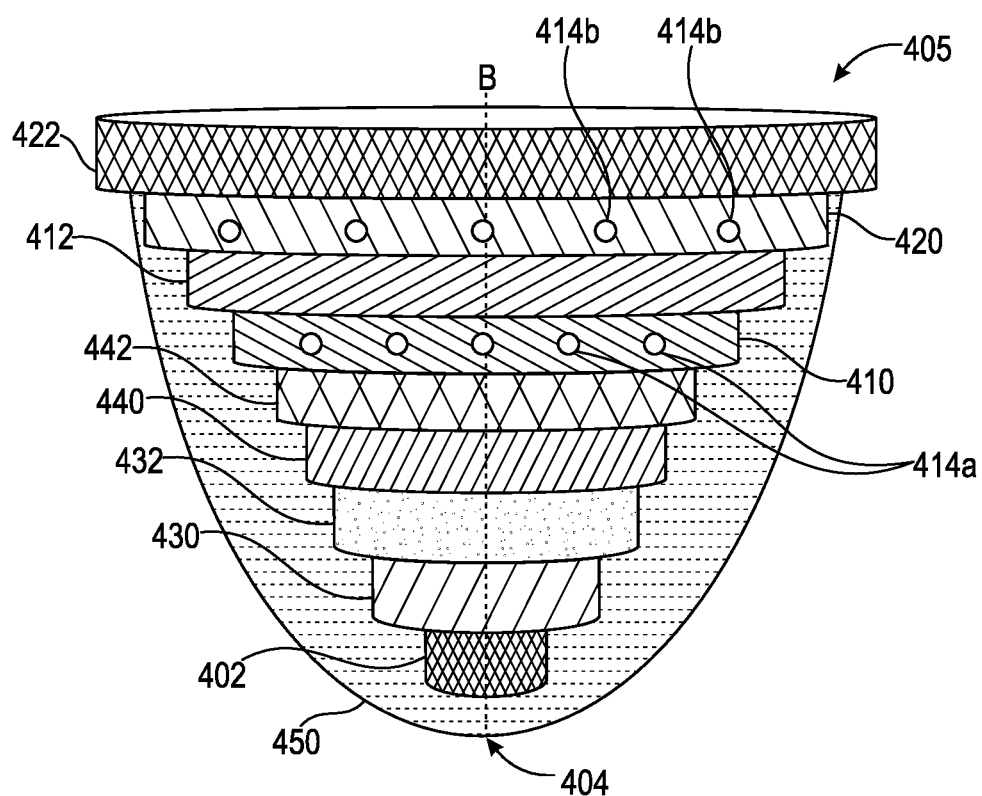

Illustrative sensor configurations having multiple working electrodes, specifically two working electrodes, are described in further detail in reference to FIGS. 4-5C. Although the following description is primarily directed to sensor configurations having two working electrodes, it is to be appreciated that more than two working electrodes may be incorporated through extension of the disclosure herein. Additional working electrodes may be used to impart additional sensing capabilities to the analyte sensors beyond just a first analyte and a second analyte.

FIG. 4 shows a cross-sectional diagram of an illustrative analyte sensor configuration having two working electrodes, a reference electrode and a counter electrode, which is compatible for use in the disclosure herein. As shown, analyte sensor 300 includes working electrodes 304 and 306 disposed upon opposite faces of substrate 302. First active area 310a is disposed upon the surface of working electrode 304, and second active area 310b is disposed upon the surface of working electrode 306. Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 may overcoat at least active areas 310a and 310b, according to various embodiments, with other components of analyte sensor 300 or the entirety of analyte sensor 300 optionally being overcoated with membrane 340 as well. Again, membrane 340 may vary compositionally at active areas 310a and 310b, if needed, in order to afford suitable permeability values for differentially regulating the analyte flux at each location. For example, membrane 340 may be homogeneous where it overcoats active area 310a and heterogeneous where it overcoats active area 310b.

Alternative sensor configurations having multiple working electrodes and differing from the configuration shown in FIG. 4 may feature a counter/reference electrode instead of separate counter and reference electrodes 320,321, and/or feature layer and/or membrane arrangements varying from those expressly depicted. For example, the positioning of counter electrode 320 and reference electrode 321 may be reversed from that depicted in FIG. 4. In addition, working electrodes 304 and 306 need not necessarily reside upon opposing faces of substrate 302 in the manner shown in FIG. 4. Instead, working electrodes 304 and 306 may reside upon the same face of substrate 302 and be spaced apart from one another with a gap in between. In particular, working electrode 304 may be positioned more toward the distal end (tip) of the analyte sensor compared to working electrode 306, which may be positioned more toward the proximal end. With a sufficiently large gap present between working electrodes 304 and 306, membrane 340 may be deposited upon working electrodes 304 and 306 through sequential dip coating operations, wherein the composition of membrane 340 may vary locally. In particular, a first dip coating operation may deposit a first membrane polymer upon both working electrodes 304 and 306, and a second dip coating operation may deposit a second membrane polymer having a different composition only upon working electrode 304, thereby defining a bilayer upon working electrode 304 and leaving a homogeneous membrane upon working electrode 306. Thus, a lower layer of the bilayer membrane and the homogeneous membrane may comprise the same membrane polymer. Alternately, a first dip coating operation may deposit a first membrane polymer upon working electrode 304 and a second dip coating operation may deposit a second membrane polymer having a different composition upon both working electrodes 304 and 306, to define the bilayer membrane and the homogeneous membrane. In this case, an upper layer of the bilayer membrane and the homogeneous membrane may comprise the same membrane polymer.

The size of the gap between working electrodes 304 and 306 is at least sufficient to afford electrical isolation between the two electrodes, and more typically is sufficient to facilitate sequential dip coating operations (e.g., by allowing the analyte sensor to be dipped to different depths to overcoat one of the working electrodes preferentially in at least one dipping step). In other words, the size of the gap may provide a margin of error for lowering the analyte sensor into a particular dip coating formulation to a specified depth to facilitate membrane deposition upon one of the working electrodes in preference to the other.

Although suitable sensor configurations may feature electrodes that are substantially planar in character, including planar sensor configurations having spaced apart working electrodes, it is to be appreciated that sensor configurations featuring non-planar electrodes may be advantageous and particularly suitable for use in the disclosure herein. In particular, cylindrical electrodes that are disposed concentrically with respect to one another and are spaced apart along the length of the sensor tail may facilitate deposition of a mass transport limiting membrane having compositional variation, as described hereinbelow. In particular, concentric working electrodes that are spaced apart along the length of a sensor tail may facilitate membrane deposition through sequential dip coating operations, in a similar manner to that described above for substantially planar sensor configurations. FIGS. 5A-5C show perspective views of analyte sensors featuring two working electrodes that are disposed concentrically with respect to one another. It is to be appreciated that sensor configurations having a concentric electrode disposition but lacking a second working electrode are also possible in the present disclosure.

FIG. 5A shows a perspective view of an illustrative sensor configuration in which multiple electrodes are substantially cylindrical and are disposed concentrically with respect to one another about a central substrate. As shown, analyte sensor 400 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400. This arrangement of electrodes may allow membrane 450 to be deposited through sequential dip coating operations to place a bilayer membrane portion on working electrode 410 and a homogenous membrane portion on working electrode 420, as discussed below. The bilayer membrane portion and the homogeneous membrane portion may be contiguous with one another.

Referring still to FIG. 5A, first active areas 414a and second active areas 414b, which are responsive to different analytes, are disposed upon the exposed surfaces of working electrodes 410 and 420, respectively, thereby allowing contact with a fluid to take place for sensing. Although active areas 414a and 414b have been depicted as three discrete spots in FIG. 5A, it is to be appreciated that fewer or greater than three spots, including a continuous layer of active area, may be present in alternative sensor configurations.

In FIG. 5A, sensor 400 is partially coated with membrane 450 upon working electrodes 410 and 420 and active areas 414a and 414b that are disposed thereon. FIG. 5B shows an alternative sensor configuration in which the substantial entirety of sensor 401 is overcoated with membrane 450. Membrane 450 may be the same or vary compositionally at active areas 414a and 414b. For example, membrane 450 may comprise a bilayer membrane portion overcoating active areas 414a and be a homogeneous membrane portion overcoating active areas 414b. Membrane 450 may be deposited through sequential dip coating operations to deposit a bilayer membrane portion upon working electrode 410 and active areas 414a and a homogeneous membrane portion upon working electrode 420 and active areas 414b.

It is to be further appreciated that the positioning of the various electrodes in FIGS. 5A and 5B may differ from that expressly depicted. For example, the positions of counter electrode 430 and reference electrode 440 may be reversed from the depicted configurations in FIGS. 5A and 5B. Similarly, the positions of working electrodes 410 and 420 are not limited to those that are expressly depicted in FIGS. 5A and 5B. FIG. 5C shows an alternative sensor configuration to that shown in FIG. 5B, in which sensor 405 contains counter electrode 430 and reference electrode 440 that are located more proximal to sensor tip 404 and working electrodes 410 and 420 that are located more distal to sensor tip 404. Sensor configurations in which working electrodes 410 and 420 are located more distal to sensor tip 404 may be advantageous by providing a larger surface area for deposition of active areas 414a and 414b (five discrete sensing spots illustratively shown in FIG. 5C), thereby facilitating an increased signal strength in some cases. Again, by having working electrodes 410 and 420 concentric with one another and spaced apart along the sensor tail, a bilayer membrane portion may be deposited upon the working electrode located closer to sensor tip 404 and a homogeneous membrane portion may be deposited upon the working electrode further from sensor tip 404 through sequential dip coating operations. Similarly, central substrate 402 may be omitted in any concentric sensor configuration disclosed herein, wherein the innermost electrode may instead support subsequently deposited layers.

It is to be appreciated that analyte sensors capable of low potential operation in accordance with the disclosure below may also feature a mass transport limiting membrane having a bilayer membrane portion and a homogeneous membrane portion. Sequential dip coating operations may be advantageous for depositing such mass transport limiting membranes. However, the present disclosure also contemplates analyte sensors in which detection need not necessarily take place at low potential, but which still incorporate a mass transport limiting membrane comprising a bilayer membrane portion and a homogeneous membrane portion.

Accordingly, analyte sensors capable of low potential operation according to the present disclosure may comprise a sensor tail comprising at least a first working electrode; a first active area disposed upon a surface of the first working electrode and responsive at low potential to a first analyte, the first active area comprising a first polymer, a first redox mediator covalently bonded to the first polymer, and at least one enzyme responsive to the first analyte covalently bonded to the first polymer; and a mass transport limiting membrane permeable to the first analyte that overcoats at least the first active area. As used herein, the term "low potential" refers to a potential above the oxidation-reduction potential of the first redox mediator and below about +200 mV, as measured relative to a Ag/AgCl reference, including below about +100 mV, below about −50 mV, below about −80 mV or below about −100 mV. Illustrative oxidation-reduction potentials of the first redox mediator that may facilitate operation at such working electrode potentials may be below about −200 mV, such as about −400 mV to about −200 mV, or from about −350 mV to about −250 mV, or from about −300 mV to about −250 mV, as measured relative to a Ag/AgCl reference.

Suitable examples of the first redox mediator capable of facilitating low-potential operation may have a structure represented by Formula 1

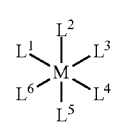

Formula 1 wherein M is osmium, ruthenium, vanadium, cobalt, or iron, $L^1$-$L^6$ are independently a heteroaromatic ligand coordinatively bound to M, two or more of which may be optionally bound together to form a bidentate, tridentate, of higher denticity ligand, at least one of $L^1$-$L^6$ contains a linking group bonding the first redox mediator to the first polymer and a least one of $L^1$-$L^6$ is functionalized with an electron-donating group. The electron-donating group is separate and distinct from the linking group.

Particularly suitable bidentate ligands featuring heteroaromatic ligands for inclusion in low-potential redox mediators include optionally substituted 2,2'-biimidazole, 2-(2-pyridyl)imidazole and 2,2'-bipyridine ligands.

Examples of 2,2'-biimidazole ligands are illustrated by Formula 2

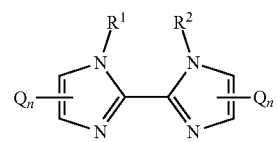

Formula 2 wherein $R^1$ and $R^2$ are independently selected from among optionally substituted alkyl, alkenyl, or aryl groups. In more specific examples, $R^1$ and $R^2$ can be independently selected from unsubstituted $C_1$ to $C_{12}$ alkyl groups or unsubstituted $C_1$ to $C_4$ alkyl groups. In some embodiments, both $R^1$ and $R^2$ are methyl. Q is optional substitution attached to one or more of the carbon atoms of the imidazole rings (n=0, 1 or 2), wherein the optional Q substitution may be an electron-donating group or linking group, in some embodiments. Suitable electron-donating groups that may comprise one or more of Q include, for example, alkyl, alkoxy, hydroxyl, amino, alkylamino, dialkylamino, or the like. If Q is not present, the carbon atom bears an H atom.

Examples of 2-(2-pyridyl)imidazole ligands may have a structure represented by Formula 3

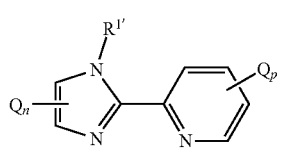

Formula 3 wherein $R^{1'}$ is an optionally substituted alkyl, alkenyl, or aryl groups, such as an unsubstituted $C_1$ to $C_{12}$ alkyl group, or $C_1$ to $C_4$ alkyl group, particularly methyl. Q is optional substitution attached to one or more of the carbon atoms of the imidazole ring or the pyridine ring (n=0, 1 or 2 for imidazole, and p=0, 1, 2, 3 or 4 for pyridine), wherein the optional Q substitution may be an electron-donating group or linking group, in some embodiments. Suitable electron-donating groups that may comprise one or more of Q include, for example, alkyl, alkoxy, hydroxyl, amino, alkylamino, dialkylamino, or the like. If Q is not present, the carbon atom bears an H atom.

Examples of 2,2'-bipyridine ligands may have a structure represented by Formula 4

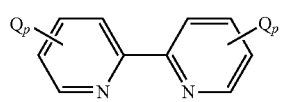

Formula 4 wherein Q is optional substitution attached to one or more of the carbon atoms of the pyridine ring (p=0, 1, 2, 3 or 4), wherein the optional Q substitution may be an electron-donating group or linking group, in some embodiments. Suitable electron-donating groups that may comprise one or more of Q include, for example, alkyl, alkoxy, hydroxyl, amino, alkylamino, dialkylamino, or the like. If Q is not present, the carbon atom bears an H atom.

Particularly suitable examples of redox mediators capable of promoting electron transfer at low potential may have a structure represented by Formula 5, wherein $L^1$ and $L^2$, $L^3$ and $L^4$, and $L^5$ and $L^6$ are each linked to form bidentate ligands, one of the bidentate ligands bears a linking group G covalently bonding the redox mediator to a polymer, and at least one of $L^1$-$L^2$, $L^3$-$L^4$, and $L^5$-$L^6$ bears a electron-donating group. The electron-donating group is separate and distinct from the linking group. The electron-donating group may be on the same bidentate ligand containing linking group G or a different bidentate ligand. $L^1$-$L^2$, $L^3$-$L^4$, and $L^5$-$L^6$ may be include bidentate ligands represented by one or more of Formulas 2-4, for example.

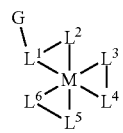

Formula 5

In some embodiments, the redox mediator may be positively charged (e.g., with a charge ranging from +1 to +5). The redox mediators can, alternatively, be negatively charged (e.g., with a charge ranging from −1 to −5), for example, when the ligands or the backbone are derivatized with a sufficient number of negatively charged functional groups such as carboxylate, phosphate or sulfonate functions. One or more counter ions can be used to balance the charge. Examples of suitable counter ions include anions, such as halide (e.g., fluoride, chloride, bromide or iodide), sulfate, phosphate, hexafluorophosphate, and tetrafluoroborate, and cations, particularly monovalent cations such as lithium, sodium, potassium, tetralkylammonium, and ammonium.

In more particular examples, the redox mediator in the first active area may have a structure represented by Formula 6

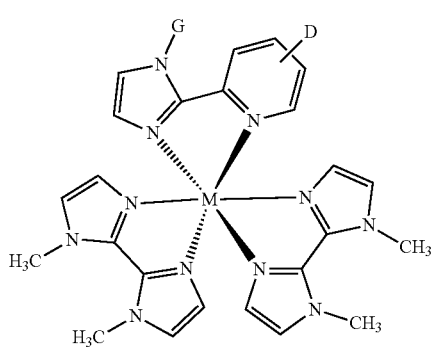

Formula 6 wherein G is a linking group covalently bonding the redox mediator to the polymer of the active area, and D is an electron donating group. Particular examples of suitable electron-donating groups include, for example, hydroxyl, alkoxy (e.g., methoxy or ethoxy), amino, or alkyl or dialkyamino (e.g., methylamino, ethylamino, dimethylamino, or diethylamino). In still more particular examples, the electron-donating group may be located at the 4-position of the pyridine ring, as shown in Formula 7.

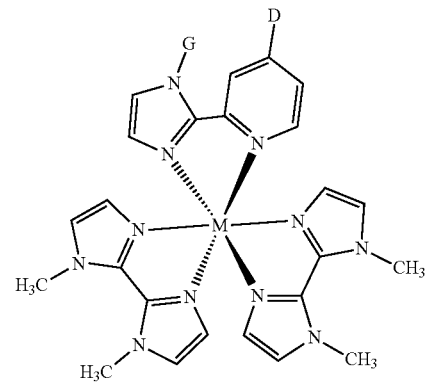

Formula 7

In any embodiment herein, the redox mediator capable of promoting electron transfer at low potential may have a structure represented by Formula 8.

Formula 8

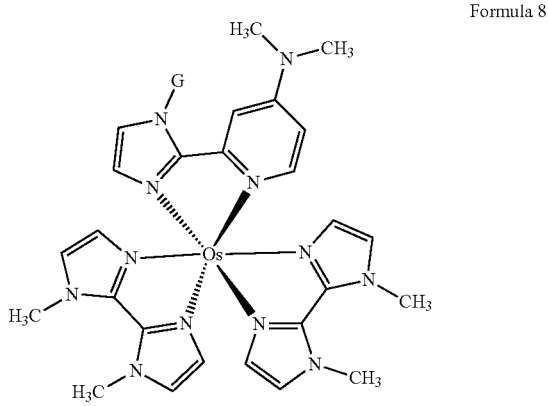

In at least one embodiment, linking group G may contain a reactive group for promoting covalent bonding to the polymer. This reactive group can react with a complementary reactive group disposed on the polymer or within a precursor to the polymer to promote covalent bonding thereto. An amide group may be present within linking group G, in some embodiments.

Any suitable polymeric backbone may be present in the active area for facilitating low-potential detection of an analyte through covalent bonding of the redox mediator and the enzyme thereto. Examples of suitable polymers within the active area include poly(4-vinylpyridine) and poly(N-vinylimidazole) or a copolymer thereof, for example, in which quaternized pyridine and imidazole groups serve as a point of attachment for the redox mediator or enzyme thereto. Other suitable polymers that may be present in the active area include, but are not limited to, those described in U.S. Pat. No. 6,605,200, incorporated herein by reference in its entirety, such as poly(acrylic acid), styrene/maleic anhydride copolymer, methylvinylether/maleic anhydride copolymer (GANTREZ polymer), poly(vinylbenzylchloride), poly(allylamine), polylysine, poly(4-vinylpyridine) quaternized with carboxypentyl groups, and poly(sodium 4-styrene sulfonate).

Enzymes covalently bound to the polymer in the first active area that are capable of promoting low-potential detection are not believed to be particularly limited. Suitable enzymes may include those capable of detecting glucose, lactate, ketones, creatinine, or the like. In some instances, the at least one enzyme covalently bound to the polymer in the first active area may comprise multiple enzymes that are collectively responsive to the analyte at low potential. Enzyme systems may be particularly desirable for detecting ketones and creatinine.

Figure 6A:
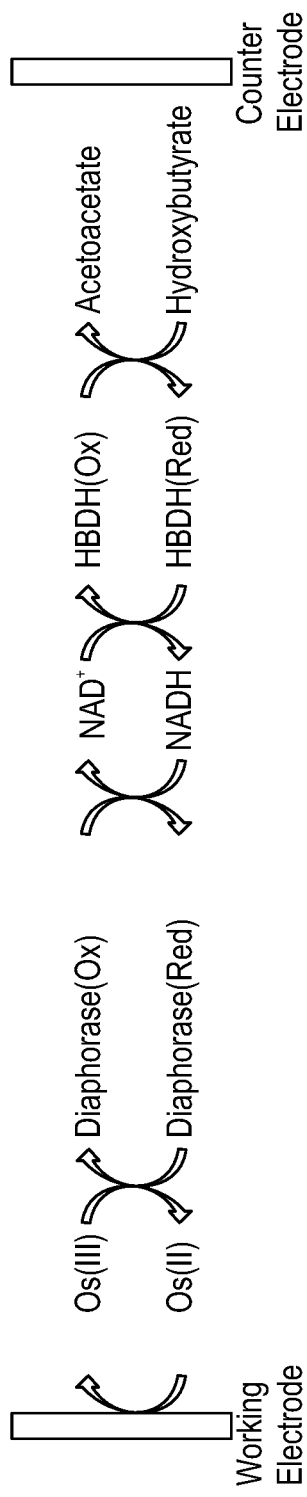
FIGS. 6A-6C show diagrams of enzyme systems that may be used for detecting ketones in an analyte sensor.
Figure 6B:
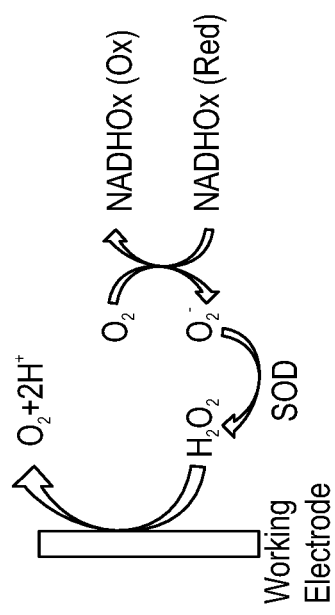
Figure 6C:
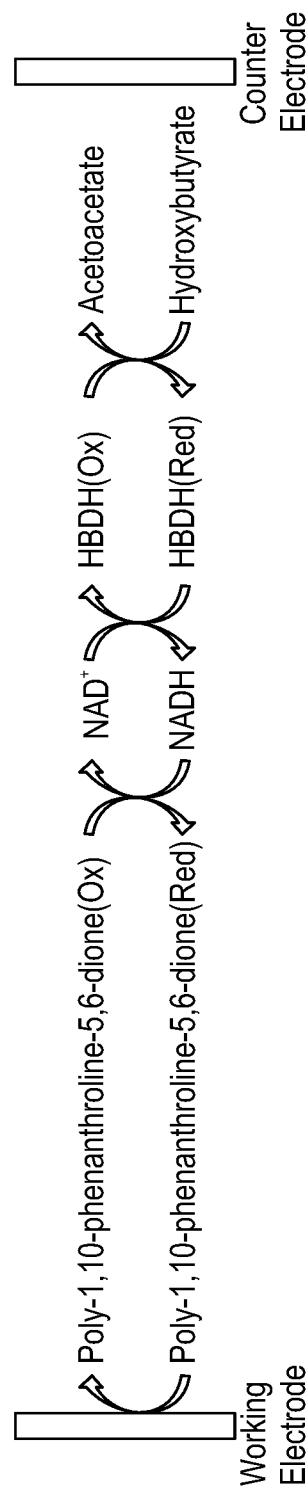

In more specific embodiments, the first active area may comprise an enzyme system capable of detecting ketones. As referenced previously, ketones are usually present in low biological abundance and may benefit from detection at low potential in accordance with the disclosure herein. Referring now to FIGS. 6A-6C, particular enzyme systems that may be used for detecting ketones will be described in further detail. In the depicted enzymatic reactions, β-hydroxybutyrate serves as a surrogate for ketones formed in vivo. As shown in FIG. 6A, one pair of concerted enzymes that may be used for detecting ketones according to the disclosure herein is β-hydroxybutyrate dehydrogenase (HBDH) and diaphorase, which may be deposited within a ketones-responsive active area upon the surface of at least one working electrode, as described further herein. When a ketones-responsive active area contains this pair of concerted enzymes, β-hydroxybutyrate dehydrogenase may convert β-hydroxybutyrate and oxidized nicotinamide adenine dinucleotide (NAD$^+$) into acetoacetate and reduced nicotinamide adenine dinucleotide (NADH), respectively. The enzyme cofactors NAD$^+$ and NADH aid in promoting the concerted enzymatic reactions disclosed herein. The NADH may then undergo oxidation under diaphorase mediation, with the electrons transferred during this process providing the basis for ketone detection at the working electrode. Thus, there is a 1:1 molar correspondence between the amount of electrons transferred to the working electrode and the amount of β-hydroxybutyrate converted, thereby providing the basis for ketones detection and quantification based upon the measured amount of current at the working electrode. Transfer of the electrons resulting from NADH oxidation to the working electrode may take place through the redox mediator capable of promoting operation at low potential. Albumin may be present as a stabilizer with this pair of concerted enzymes. According to particular embodiments, the β-hydroxybutyrate dehydrogenase and the diaphorase may be covalently bonded to a polymer within the ketones-responsive active area of the analyte sensors. The NAD$^+$ may or may not be covalently bonded to the polymer, but if the NAD$^+$ is not covalently bonded, it may be physically retained within the ketones-responsive active area. A membrane overcoating the ketones-responsive active area may aid in retaining the NAD$^+$ within the ketones-responsive active area while still permitting sufficient inward diffusion of ketones to permit detection thereof.

Other suitable chemistries for enzymatically detecting ketones are shown in FIGS. 6B and 6C. In both instances, there is again a 1:1 molar correspondence between the amount of electrons transferred to the working electrode and the amount of β-hydroxybutyrate converted, thereby providing the basis for ketones detection.

As shown in FIG. 6B, β-hydroxybutyrate dehydrogenase (HBDH) may again convert β-hydroxybutyrate and NAD$^+$ into acetoacetate and NADH, respectively. Instead of electron transfer to the working electrode being completed by diaphorase (see FIG. 6A) and a suitable redox mediator, the reduced form of NADH oxidase (NADHOx (Red)) undergoes a reaction to form the corresponding oxidized form (NADHOx (Ox)). NADHOx (Red) may then reform through a reaction with molecular oxygen to produce superoxide, which may undergo subsequent conversion to hydrogen peroxide under superoxide dismutase (SOD) mediation. The hydrogen peroxide may then undergo oxidation at the working electrode to provide a signal that may be correlated to the amount of ketones that were initially present. The SOD may be covalently bonded to a polymer in the ketones-responsive active area, according to various embodiments. Like the enzyme system shown in FIG. 6A, the β-hydroxybutyrate dehydrogenase and the NADH oxidase may be covalently bonded to a polymer in the ketones-responsive active area, and the NAD may or may not be covalently bonded to a polymer in the ketones-responsive active area. If the NAD$^+$ is not covalently bonded, it may be physically retained within the ketones-responsive active area, with a membrane polymer promoting retention of the NAD$^+$ within the ketones-responsive active area.

As shown in FIG. 6C, another enzymatic detection chemistry for ketones may utilize β-hydroxybutyrate dehydrogenase (HBDH) to convert β-hydroxybutyrate and NAD$^+$ into acetoacetate and NADH, respectively. The electron transfer cycle in this case is completed by oxidation of 1,10-phenanthroline-5,6-dione at the working electrode to reform NAD. The 1,10-phenanthroline-5,6-dione may or may not be covalently bonded to a polymer within the ketones-responsive active area. Like the enzyme system shown in FIG. 6A, the β-hydroxybutyrate dehydrogenase may be covalently bonded to a polymer in the ketones-responsive active area, and the NAD may or may not be covalently bonded to a polymer in the ketones-responsive active area. Inclusion of an albumin in the active area may provide a surprising improvement in response stability. A suitable membrane polymer may promote retention of the $NAD^+$ within the ketones-responsive active area.

Analyte sensors of the present disclosure may be further configured to analyze for a second or subsequent analyte in addition to the analyte detectable in the first active area at low potential. To facilitate detection of a second analyte, the analyte sensors of the present disclosure may further comprise a second working electrode, and a second active area disposed upon a surface of the second working electrode and responsive to a second analyte differing from the first analyte, the second active area comprising a second polymer, a second redox mediator differing from the first redox mediator covalently bonded to the second polymer, and at least one enzyme responsive to the second analyte covalently bonded to the second polymer. A second portion of the mass transport limiting membrane may overcoat the second active area. The at least one enzyme responsive to the second analyte may comprise an enzyme system including multiple enzymes that are collectively responsive to the second analyte. The second redox mediator in the second active area need not necessarily be capable of promoting electron transfer at a low potential, although it may be.

Suitable redox mediators for inclusion in the second active area may include, but are not limited to osmium complexes and other transition metal complexes, such as those described in U.S. Pat. Nos. 6,134,461 and 6,605,200, which are incorporated herein by reference in their entirety. Additional examples of suitable redox mediators include those described in U.S. Pat. Nos. 6,736,957, 7,501,053 and 7,754,093, the disclosures of each of which are also incorporated herein by reference in their entirety. Other suitable redox mediators for inclusion in the second active area may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl(imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

The active areas for promoting analyte detection according to the disclosure herein may comprise a polymer to which the redox mediators are covalently bound. Suitable examples of polymer-bound redox mediators may include those described in U.S. Pat. Nos. 8,444,834, 8,268,143 and 6,605,201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. The polymer within each active area may be the same or different.

In a particular example, the second active area may be configured to detect glucose in combination with the analyte detectable at low potential in the first active area. As such, the second enzyme may be glucose oxidase in particular embodiments of the present disclosure. In still more particular examples, the first analyte may be ketones, detectable by an enzyme system as described herein, and the second analyte may be glucose, detectable by glucose oxidase.

Detection of each analyte may comprise applying a potential to each working electrode separately, such that separate signals are obtained from each analyte. The signal obtained from each analyte may then be correlated to an analyte concentration through use of a calibration curve or function, or by employing a lookup table. Correlation of the analyte signal to an analyte concentration may be conducted through use of a processor in particular examples.

In other analyte sensor configurations, the first active area and the second active area may be disposed upon a single working electrode. A first signal may be obtained from the first active area at a low potential, and a second signal containing a signal contribution from both active areas may be obtained at a higher potential. Subtraction of the first signal from the second signal may then allow the signal contribution arising from the second analyte to be determined. The signal contribution from each analyte may then be correlated to an analyte concentration in a similar manner to that described for sensor configurations having multiple working electrodes.

Accordingly, the present disclosure provides methods comprising: providing an analyte sensor comprising: a sensor tail comprising at least a first working electrode; a first active area disposed upon a surface of the first working electrode and responsive at low potential to the first analyte, the first active area comprising a first polymer, a first redox mediator covalently bonded to the first polymer, and at least one enzyme responsive to the first analyte covalently bonded to the first polymer, wherein the redox mediator has a structure presented by any one of Formulas 1-8, as described above, wherein G is a linking group covalently bonding the first redox mediator to the first polymer; and a mass transport limiting membrane permeable to the first analyte that overcoats at least the first active area; applying a low potential to the first working electrode; obtaining a first signal at or above an oxidation-reduction potential of the first active area, the first signal being proportional to a concentration of a first analyte in a fluid contacting the first active area; and correlating the first signal to the concentration of the first analyte in the fluid.

The low potential may be below about +200 mV, as measured relative to a Ag/AgCl reference, including below about +100 mV, below about −50 mV, below about −80 mV or below about −100 mV. The low potential may also be above the oxidation-reduction potential of the first redox mediator. Illustrative oxidation-reduction potentials of the first redox mediator that may facilitate operation a low working electrode potential may be below about −200 mV, such as about −400 mV to about −200 mV, or from about −350 mV to about −250 mV, or from about −300 mV to about −250 mV, as measured relative to a Ag/AgCl reference.

The analyte sensors disclosed herein further include a mass transport limiting membrane permeable to an analyte that overcoats at least the first active area. When multiple active areas are present, the mass transport limiting membrane may overcoat each active area, including the option of compositional variation upon differing active areas, such as may be achieved through sequential dip coating operations to produce a bilayer membrane portion upon a working electrode located closer to the sensor tip. The mass transport limiting membrane may comprise a membrane polymer, such as a polyvinylpyridine or polyvinylimidazole homopolymer or copolymer, which may be further crosslinked with a suitable crosslinking agent. The membrane polymer may comprise a copolymer of vinylpyridine and styrene in particular embodiments. In more particular examples, a membrane polymer overcoating one or more active areas may be crosslinked with a branched crosslinker comprising three or more crosslinkable groups, such as polyethyleneglycol tetraglycidyl ether, which may surprisingly decrease the amount of extractables obtainable from the mass transport limiting membrane, as referenced above. Still more particularly, the mass transport limiting membrane may comprise polyvinylpyridine or a copolymer of vinylpyridine and styrene crosslinked with a branched glycidyl ether crosslinker comprising three crosslinkable groups, such as polyethylene glycol tetraglycidyl ether. In particular, the epoxide groups of the polyethylene glycol tetraglycidyl ether may react with a pyridine nitrogen atom or an imidazole nitrogen atom promote covalent bonding of the crosslinker via epoxide ring opening. A hydroxyalkyl group bridging a body of the crosslinker to the heterocycle of the membrane polymer may result.

A suitable copolymer of vinylpyridine and styrene may have a styrene content ranging from about 0.01% to about 50% mole percent, or from about 0.05% to about 45% mole percent, or from about 0.1% to about 40% mole percent, or from about 0.5% to about 35% mole percent, or from about 1% to about 30% mole percent, or from about 2% to about 25% mole percent, or from about 5% to about 20% mole percent. Substituted styrenes may be used similarly and in similar amounts. A suitable copolymer of vinylpyridine and styrene may have a molecular weight of 5 kDa or more, or about 10 kDa or more, or about 15 kDa or more, or about 20 kDa or more, or about 25 kDa or more, or about 30 kDa or more, or about 40 kDa or more, or about 50 kDa or more, or about 75 kDa or more, or about 90 kDa or more, or about 100 kDa or more. In non-limiting examples, a suitable copolymer of vinylpyridine and styrene may have a molecular weight ranging from about 5 kDa to about 150 kDa, or from about 10 kDa to about 125 kDa, or from about 15 kDa to about 100 kDa, or from about 20 kDa to about 80 kDa, or from about 25 kDa to about 75 kDa, or from about 30 kDa to about 60 kDa.

Accordingly, at least some of the analyte sensors described herein may comprise a sensor tail comprising at least a first working electrode, a first active area disposed upon a surface of the first working electrode, and a mass transport limiting membrane permeable to the first analyte that overcoats at least the first active area. The first active area comprises a first polymer and at least one enzyme covalently bonded to the first polymer and responsive to a first analyte. The mass transport limiting membrane comprises a membrane polymer crosslinked with a branched glycidyl ether crosslinker comprising three or more crosslinkable groups, such as polyethylene glycol tetraglycidyl ether.

The crosslinking may be intermolecular in more particular embodiments. The polyethylene glycol tetraglycidyl ether used to promote intermolecular crosslinking between two or more membrane polymer backbones may exhibit a broad range of suitable molecular weights. Up to four polymer backbones may crosslinked with a single molecule of the polyethylene glycol tetraglycidyl ether crosslinker. In particular examples, the molecular weight of the polyethylene glycol tetraglycidyl ether may range from about 1000 g/mol to about 5000 g/mol. The number of ethylene glycol repeat units in each arm of the polyethylene glycol tetraglycidyl ether may be the same or different, and may typically vary over a range within a given sample to afford an average molecular weight. The structure of the polyethylene glycol tetraglcidyl ether prior to crosslinking may be represented by Formula 9 below Formula 9

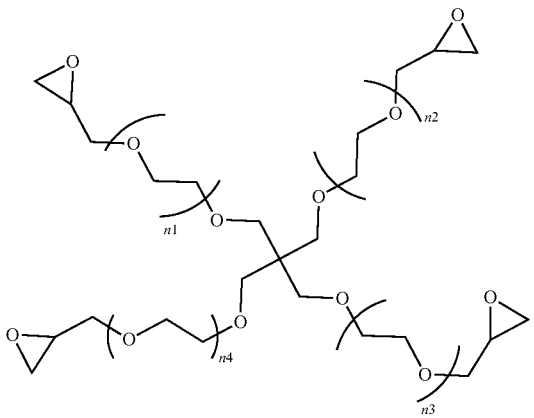

wherein n1, n2, n3 and n4 are each an integer greater than or equal to 0, usually 1 or greater, and n1, n2, n3 and n4 may be the same or different. A sum of n1, n2, n3 and n4 may be selected such that the molecular weight of the polyethylene glycol tetraglycidyl ether falls within the foregoing range. In other words, to produce a polyethylene glycol tetraglycidyl ether having a molecular weight within the foregoing range, a sum of n1, n2, n3 and n4 may range from about 14 to about 110, or about 15 to about 104, including any sub-range in between these values, wherein n1, n2, n3 and n4 may independently be any integer greater than or equal to 0 or greater than or equal to 1.

Crosslinking density refers to the number of membrane polymer side chains that have a crosslinker attached thereto. Membrane polymers crosslinked with a branched glycidyl ether, such as polyethylene glycol tetraglycidyl ether or a similar polyethylene oxide crosslinker having three or more crosslinkable groups, may have a crosslinking density varying over a wide range. In particular examples, the fraction of side chains that may have a crosslinker appended thereto may be about 0.1% or above of the available heterocycles in the membrane polymer, or about 0.2% or above of the available heterocycles in the membrane polymer, or about 0.3% or above of the available heterocycles in the membrane polymer, or about 0.4% or above of the available heterocycles in the membrane polymer, or about 0.5% or above of the available heterocycles in the membrane polymer, or about 0.6% or above of the available heterocycles in the membrane polymer, or about 0.7% or above of the available heterocycles in the membrane polymer, or about 0.8% or above of the available heterocycles in the membrane polymer, or about 0.9% or above of the available heterocycles in the membrane polymer, or about 1.0% or above of the available heterocycles in the membrane polymer, or about 1.2% or above of the available heterocycles in the membrane polymer, or about 1.4% or above of the available heterocycles in the membrane polymer, or about 1.6% or above of the available heterocycles in the membrane polymer, or about 1.8% or above of the available heterocycles in the membrane polymer, or about 2.0% or above of the available heterocycles in the membrane polymer, or about 2.2% or above of the available heterocycles in the membrane polymer, or about 2.4% or above of the available heterocycles in the membrane polymer, or about 2.6% or above of the available heterocycles in the membrane polymer, or about 2.8% or above of the available heterocycles in the membrane polymer, or about 3.0% or above of the available heterocycles in the membrane polymer, or about 3.5% or above of the available heterocycles in the membrane polymer, or about 4.0% or above of the available heterocycles in the membrane polymer, or about 4.5% or above of the available heterocycles in the membrane polymer, or about 5.0% or above of the available heterocycles in the membrane polymer, or about 5.5% or above of the available heterocycles in the membrane polymer, or about 6.0% or above of the available heterocycles in the membrane polymer, or about 6.5% or above of the available heterocycles in the membrane polymer, or about 7.0% or above of the available heterocycles in the membrane polymer, or about 7.5% or above of the available heterocycles in the membrane polymer, or about 8.0% or above of the available heterocycles in the membrane polymer, or about 8.5% or above of the available heterocycles in the membrane polymer, or about 9.0% or above of the available heterocycles in the membrane polymer, or about 9.5% or above of the available heterocycles in the membrane polymer, or about 10% or above of the available heterocycles in the heterocyclic polymer. In more specific embodiments, the crosslinker may be appended to between about 1% and about 20% of the available heterocycles in the membrane polymer, or between about 2% and about 10% of the available heterocycles in the membrane polymer, or between about 3% and about 8% of the available heterocycles in the membrane polymer, or between about 4% and about 9% of the available heterocycles in the membrane polymer, or between about 5% and about 12% of the available heterocycles in the membrane polymer.

Suitable membrane polymers may further include one or more polyether arms (side chains) that are bonded to the nitrogen atom of the pyridine or imidazole monomer units. Any of the membrane polymers disclosed herein may further comprise one or more polyether arms. Polyether arms are distinguished from the crosslinking group formed from polyethylene glycol tetraglycidyl ether or a similar crosslinker in that the polyether arm does not extend between separate polymer chains or terminate intramolecularly within a single polymer chain. Thus, polyether arms are separate and distinct from the crosslinking group formed from the crosslinker. Polyether arms may comprise a polyethylene oxide block and a polypropylene oxide block, particularly a polyether arm having a polypropylene oxide block inserted between two polyethylene oxide blocks. Bonding of the polyether arm to a heterocyclic nitrogen atom may occur through any reactive functional group capable of forming a bond to the nitrogen atom of the heterocycle in the membrane polymer. Bonding of the polyether arm to the heterocyclic nitrogen atom may be through an alkyl group, a hydroxyl-functionalized alkyl group, or a carbonyl. The polyether arm may also contain an amine group remote from the heterocyclic nitrogen atom or be amine-free in other particular instances.

The polyether arms of the membrane polymer may comprise at least one polyethylene oxide block and at least one polypropylene oxide block, thereby affording at least a diblock arrangement of polyethylene oxide and polypropylene oxide monomer units bound via a spacer to a heterocyclic nitrogen atom. Either the polyethylene oxide block or the polypropylene oxide block may be bound to the spacer. In other more specific embodiments, the polyether arms may comprise, in order, a spacer, a first polyethylene oxide block, a polypropylene oxide block, and a second polyethylene oxide block (i.e., an A-B-A repeat pattern) or, in order, a spacer, a first polypropylene oxide block, a polyethylene oxide block, and a second polypropylene oxide block (i.e., a B-A-B repeat pattern). An amine group may intercede between a polyethylene oxide block and a polypropylene oxide block in amine-containing polyether arms Thus, the polyether arms in the membrane polymers described herein may have a structure generally defined by Formulas 10-13 below,

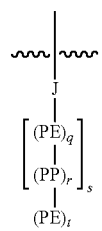

Formula 10

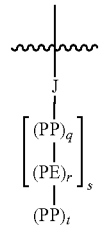

Formula 11

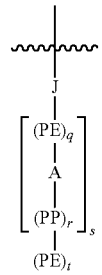

Formula 12

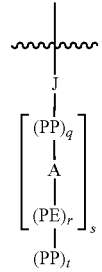

Formula 13 wherein PE represents a polyethylene oxide block, PP represents a polypropylene oxide block, A is an amine group, and J is a spacer group. Spacer group J may become bonded to a heterocycle of the membrane polymer. Suitable spacer groups J may include, but are not limited to, alkyl, hydroxy-functionalized alkyl, carbonyl, carboxylic ester, carboxamide, and the like. Variables q, r, s, and t are positive integers defining the number of monomer units in each block and the number of times the blocks are repeated, with the proviso that in diblock arrangements, variable t may be 0 and variable s may be 1. According to some embodiments, variable q is an integer ranging between about 2 and about 50 or between about 6 and about 20, variable r is an integer ranging between about 2 and about 60 or between about 10 and about 40, and variable t is an integer ranging between about 2 and about 50 or between about 10 and about 30. According to some or other various embodiments, variable s is an integer ranging between 1 and about 20 or between 1 and about 10. In some embodiments, variable s is equal to 1.

In more specific embodiments of the present disclosure, amine-free polyether arms having a triblock arrangement of polyethylene oxide, polypropylene oxide, and polyethylene oxide (corresponding to Formula 10) arm may have a structure defined by Formula 14,

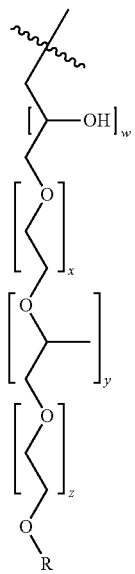

Formula 14 wherein R is an alkyl group, particularly a methyl group, variable w is 0 or 1, variable x is an integer ranging between about 4 and about 24 or between about 6 and about 20, variable y is an integer ranging between about 8 and about 60 or between about 10 and about 40, and variable z is an integer ranging between about 6 and about 36 or between about 10 and about 30. In more specific embodiments, variable x may range between about 8 and about 16 or between about 9 and about 12, variable y may range between about 10 and about 32, or between about 16 and about 30, or between about 12 and about 20, and variable z may range between about 10 and about 20 or between about 14 and about 18. In some embodiments, variable x may be less than variable z, such that the second polyethylene oxide block is longer (larger) than the first polyethylene oxide block. If variable w is 0, the amine-free polyether arm is directly bonded to the membrane polymer by a two-carbon alkyl group, although longer alkyl groups are also contemplated by the present disclosure.

In other particular embodiments of the present disclosure, polyether arms having a triblock arrangement of polyethylene oxide, polypropylene oxide, and polyethylene oxide and having an amine group interceding between a polyethylene oxide block and the polypropylene oxide block (corresponding to Formula 12) may have a structure defined by Formula 15,

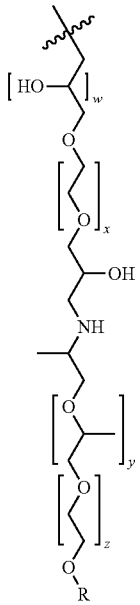

Formula 15 wherein w, x, y, z and R are defined as above for Formula 14. If variable w is 0, the polyether arm is directly bonded to the membrane polymer by a two-carbon alkyl group, although longer alkyl groups are also contemplated by the present disclosure.

The polyether arms described herein may become bonded to a heterocyclic nitrogen atom by way of a reactive functionality in a polyether arm precursor. Suitable reactive functionalities may include a halogen or an epoxide, for example. Epoxides, for example, lead to formation of a hydroxyalkyl spacer group connecting the polyether arm to a heterocyclic nitrogen atom of the membrane polymer, as exemplified in Formulas 14 and 15 above (n=1 in Formulas 14 and 15). Halogen-functionalized polyether arm precursors, in contrast, may lead to an alkyl spacer (n=0 in Formulas 14 and 15), wherein suitable alkyl groups may be straight- or branched-chain and contain 2 to about 20 carbon atoms.

In some embodiments, a sulfonate-containing arm may be appended as a side chain in at least a portion of the membrane polymers disclosed herein. The sulfonate-containing arm may be present in combination with the polyether arms and/or a crosslinker in any suitable ratio. Any of the membrane polymers disclosed herein may comprise a higher quantity of polyether arms or crosslinking groups than sulfonate-containing arms. A sulfonate-containing arm may be appended to the membrane polymer via an alkyl group. The alkyl group may contain between 1 and about 6 carbon atoms, or between 2 and about 4 carbon atoms, according to various embodiments. Suitable reagents for introducing a sulfonate-containing arm to the membrane polymers disclosed herein may include halosulfonic acid compounds such as chloromethanesulfonic acid, bromoethanesulfonic acid, or the like, or cyclic sulfonates (sultones).

Polydimethylsiloxane (PDMS) may be incorporated in any of the mass transport limiting membranes disclosed herein.

When a first active area and a second active area configured for assaying different analytes are disposed on separate working electrodes, the mass transport limiting membrane may have differing permeability values for the first analyte and the second analyte. Although the membrane thickness at each working electrode and/or the sizes of the active areas may be varied to levelize the sensitivity for each analyte, this approach may significantly complicate manufacturing of the analyte sensors. As a solution, the mass transport limiting membrane overcoating at least one of the active areas may comprise an admixture of a first membrane polymer and a second membrane polymer or a bilayer of the first membrane polymer and the second membrane polymer. A homogeneous membrane may overcoat the active area not overcoated with the admixture or the bilayer, wherein the homogeneous membrane comprises only one of the first membrane polymer or the second membrane polymer. Advantageously, the architectures of the analyte sensors disclosed herein readily allow a continuous membrane having a homogenous membrane portion to be disposed upon a first active area and a multi-component membrane portion to be disposed upon a second active area of the analyte sensors, thereby levelizing the permeability values for each analyte concurrently to afford improved sensitivity and detection accuracy. Continuous membrane deposition may take place through sequential dip coating operations in particular embodiments.

Embodiments disclosed herein include:

A. Analyte sensors capable of low potential detection of an analyte. The analyte sensors comprise: a sensor tail comprising at least a first working electrode; a first active area disposed upon a surface of the first working electrode and responsive at low potential to a first analyte, the first active area comprising a first polymer, a first redox mediator covalently bonded to the first polymer, and at least one enzyme responsive to the first analyte covalently bonded to the first polymer; wherein the first redox mediator has a structure of

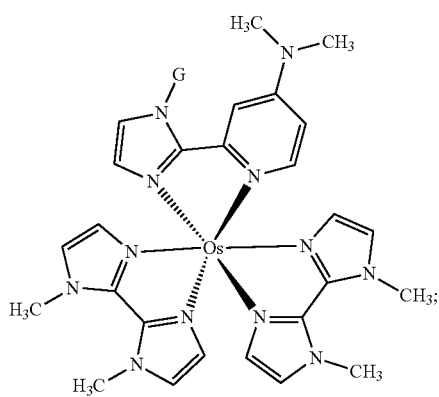

wherein G is a linking group covalently bonding the first redox mediator to the first polymer; and a mass transport limiting membrane permeable to the first analyte that overcoats at least the first active area.

B. Methods for detecting an analyte using an analyte sensor capable of low-potential detection. The methods comprise: providing an analyte sensor comprising: a sensor tail comprising at least a first working electrode; a first active area disposed upon a surface of the first working electrode and responsive at low potential to the first analyte, the first active area comprising a first polymer, a first redox mediator covalently bonded to the first polymer, and at least one enzyme responsive to the first analyte covalently bonded to the first polymer; wherein the first redox mediator has a structure of

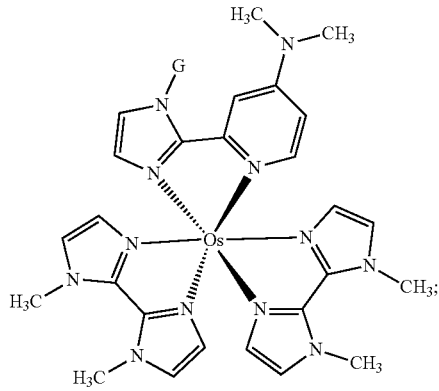

wherein G is a linking group covalently bonding the first redox mediator to the first polymer; and a mass transport limiting membrane permeable to the first analyte that overcoats at least the first active area; applying a low potential to the first working electrode; obtaining a first signal at or above an oxidation-reduction potential of the first active area, the first signal being proportional to a concentration of a first analyte in a fluid contacting the first active area; and correlating the first signal to the concentration of the first analyte in the fluid.

B1. Methods for detecting an analyte using an analyte sensor capable of low potential detection. The methods comprise: exposing an analyte sensor to a fluid comprising a first analyte; wherein the analyte sensor comprises: a sensor tail comprising at least a first working electrode; a first active area disposed upon a surface of the first working electrode and responsive at low potential to the first analyte, the first active area comprising a first polymer, a first redox mediator covalently bonded to the first polymer, and at least one enzyme responsive to the first analyte covalently bonded to the first polymer; wherein the first redox mediator has a structure of

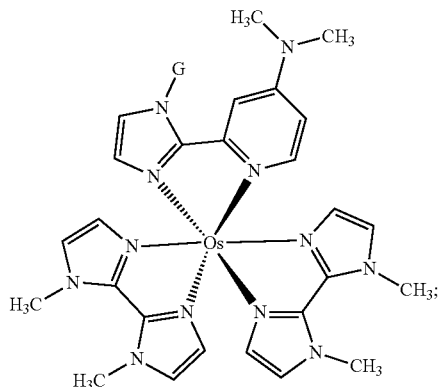

wherein G is a linking group covalently bonding the first redox mediator to the first polymer; and a mass transport limiting membrane permeable to the first analyte that overcoats at least the first active area; applying a low potential to the first working electrode; obtaining a first signal at or above an oxidation-reduction potential of the first active area, the first signal being proportional to a concentration of the first analyte in the fluid; and correlating the first signal to the concentration of the first analyte in the fluid.

C. Analyte sensors containing a mass transport limiting membrane crosslinked with branched glycidyl ether crosslinker. The analyte sensors comprise: a sensor tail comprising at least a first working electrode; a first active area disposed upon a surface of the first working electrode, the first active area comprising a first polymer and at least one enzyme covalently bonded to the first polymer and responsive to a first analyte; and a mass transport limiting membrane permeable to the first analyte that overcoats at least the first active area, the mass transport limiting membrane comprising a membrane polymer crosslinked with a branched crosslinker comprising three or more crosslinkable groups.

D. Methods for detecting an analyte using an analyte sensor containing a mass transport limiting membrane crosslinked with a branched glycidyl ether crosslinker. The methods comprise: providing an analyte sensor comprising: a sensor tail comprising at least a first working electrode; a first active area disposed upon a surface of the first working electrode, the first active area comprising a first polymer and at least one enzyme covalently bonded to the first polymer and responsive to a first analyte; and a mass transport limiting membrane permeable to the first analyte that overcoats at least the first active area, the mass transport limiting membrane comprising a membrane polymer crosslinked with a branched crosslinker comprising three or more crosslinkable groups; applying a potential to the first working electrode; obtaining a first signal at or above an oxidation-reduction potential of the first active area, the first signal being proportional to a concentration of a first analyte in a fluid contacting the first active area; and correlating the first signal to the concentration of the first analyte in the fluid.

Embodiments A-D may have one or more of the following elements in any combination.

Element 1: wherein the at least one enzyme comprises an enzyme system comprising multiple enzymes that are collectively responsive to the first analyte.

Element 2: wherein the first analyte comprises one or more ketones.

Element 3: wherein the mass transport limiting membrane comprises a membrane polymer crosslinked with a branched crosslinker comprising three or more crosslinkable groups.

Element 4: wherein the membrane polymer comprises a polyvinylpyridine or a polyvinylimidazole.

Element 5: wherein the membrane polymer comprises a copolymer of vinylpyridine and styrene.

Element 6: wherein the branched crosslinker comprises polyethyleneglycol tetraglycidyl ether.

Element 7: wherein the analyte sensor further comprises a second working electrode; and a second active area disposed upon a surface of the second working electrode and responsive to a second analyte differing from the first analyte, the second active area comprising a second polymer, a second redox mediator differing from the first redox mediator covalently bonded to the second polymer, and at least one enzyme responsive to the second analyte covalently bonded to the second polymer; wherein a second portion of the mass transport limiting membrane overcoats the second active area.

Element 8: wherein the at least one enzyme responsive to the second analyte comprises an enzyme system comprising multiple enzymes that are collectively responsive to the second analyte.

Element 9: wherein the second analyte comprises glucose.

Element 10: wherein the low potential is above an oxidation-reduction potential of the first redox mediator and below about −80 mV relative to a Ag/AgCl reference.

Element 10A: wherein the oxidation-reduction potential of the first redox mediator ranges from about −200 mV to about −400 mV relative to a Ag/AgCl reference.

Element 11: wherein the polyethylene glycol tetraglycidyl ether has a molecular weight ranging from about 1000 g/mol to about 5000 g/mol.

By way of non-limiting example, exemplary combinations applicable to A and B may include, but are not limited to, 1 and 2; 1-3; 1, 3 and 6; 1 and 4; 1 and 7; 1 and 9; 1 and 10 or 10A; 2 and 3; 2, 3 and 6; 2 and 7; 2 and 9; 2 and 10 or 10A; 3 and 4; 3 and 6; 3, 4 and 6; 3, 5 and 6; 3 and 7; 3 and 9; 3 and 10 or 10A; 4 and 7; 5 and 7; 4 or 5, and 9; and 4 or 5, and 10 or 10A. By way of further non-limiting example, exemplary combinations applicable to C and D may include, but are not limited to, 6 and 11; 4 and 6; 5 and 6; 6 and 7; 6-8; 4, 6 and 11; 5, 6 and 11; 6, 7 and 11; and 6-8 and 11.

Additional embodiments disclosed herein include:

A': Methods for forming a mass transport limiting membrane by dip coating. The methods comprise: providing an analyte sensor comprising: a sensor tail comprising at least a first working electrode and a second working electrode that are spaced apart from one another along a length of the sensor tail; and a first active area disposed upon a surface of the first working electrode and a second active area disposed upon a surface of the second working electrode, the first active area and the second active area being responsive to different analytes; and depositing a mass transport limiting membrane upon the first active area and the second active area by sequential dip coating operations; wherein the mass transport limiting membrane comprises a bilayer membrane portion overcoating the first active area and a homogeneous membrane portion overcoating the second active area.

B': Analyte sensors having a dip-coated mass transport limiting membrane. The analyte sensors comprise: a sensor tail comprising at least a first working electrode and a second working electrode that are spaced apart from one another along a length of the sensor tail; a first active area disposed upon a surface of the first working electrode and a second active area disposed upon a surface of the second working electrode, the first active area and the second active area being responsive to different analytes; and a dip-coated mass transport limiting membrane upon the first active area and the second active area, the dip-coated mass transport limiting membrane comprising a dip-coated bilayer membrane portion overcoating the first active area and a dip-coated homogeneous membrane portion overcoating the second active area.

Embodiments A' and B' may have one or more of the following elements present in any combination:

Element 1': wherein the bilayer membrane portion and the homogeneous membrane portion are contiguous with one another.

Element 2': wherein the first working electrode and the first active area are located closer to a tip of the analyte sensor than are the second working electrode and second active area.

Element 3': wherein an upper layer of the bilayer membrane portion and the homogeneous membrane portion comprise the same membrane polymer.

Element 4': wherein a first dip coating operation deposits a first membrane polymer upon the first active area and a second dip coating operation deposits a second membrane polymer upon both the first active area and the second active area to define the bilayer membrane portion upon the first active area and the homogeneous membrane portion upon the second active area, the first membrane polymer and the second membrane polymer differing from one another.

Element 5': wherein a lower layer of the bilayer membrane portion and the homogeneous membrane portion comprise the same membrane polymer.

Element 6': wherein a first dip coating operation deposits a first membrane polymer upon both the first active area and the second active area and a second dip coating operation deposits a second membrane polymer upon the first active area to define the bilayer membrane portion upon the first active area, the first membrane polymer and the second membrane polymer differing from one another.

Element 7': wherein the first active area is responsive to glucose, lactate, ketones, or creatinine.

Element 8': wherein the first active area is responsive to ketones.

Element 9': wherein the second active area is responsive to glucose.

Element 10': wherein at least a portion of the mass transport limiting membrane comprises a crosslinked polyvinylpyridine homopolymer or copolymer.

Element 11': wherein at least a portion of the mass transport limiting membrane comprises a membrane polymer crosslinked with a branched crosslinker comprising three or more crosslinkable groups.

Element 12': wherein the branched crosslinker comprises polyethyleneglycol tetraglycidyl ether.

Element 13': wherein the dip-coated bilayer membrane portion and the dip-coated homogeneous membrane portion are contiguous with one another.

Element 14': wherein the first working electrode and the first active area are located closer to a tip of the analyte sensor than are the second working electrode and the second active area.

Element 15': wherein an upper layer of the dip-coated bilayer membrane portion and the dip-coated homogeneous membrane portion comprise the same membrane polymer.

Element 16': wherein a lower layer of the dip-coated bilayer membrane portion and the dip-coated homogeneous membrane portion comprise the same membrane polymer.

Element 17': wherein the first active area is responsive to ketones.

Element 18': wherein the second active area is responsive to glucose.

By way of non-limiting example, exemplary combinations applicable to A' include, but are not limited to: 1' and 2'; 1'-3'; 1'-4'; 1', 2' and 5'; 1', 2', 5' and 6'; 1' and 7'; 1' and 8'; 1', 8' and 9'; 1' and 10'; 2' and 3'; 2'-4'; 2'-5'; 2', 5' and 6'; 2' and 7'; 2' and 8'; 2', 3', 4' and 8'; 2', 3', 4', 8' and 9'; 2', 5', 6' and 8'; 2', 5', 6', 8' and 9'; 3' and 4'; 3', 4' and 7'; 3', 4' and 8'; 3', 4', 8' and 9'; 3' and 7'; 3' and 8'; 3', 8' and 9'; 5' and 6'; 5', 6' and 8'; 5', 6', 8' and 9'; and 8' and 9'. Exemplary combinations applicable to B' include, but are not limited to, 13' and 14'; 13', 14' and 15'; 13', 14' and 16'; 13', 14' and 17'; 13', 14', 17' and 18'; 14' and 15'; 14' and 16'; 14' and 17'; 14' and 18'; 15' and 17'; 15', 17' and 18'; 16' and 17'; 16', 17' and 18'; and 17' and 18'.

To facilitate a better understanding of the disclosure herein, the following examples of various representative embodiments are given. In no way should the following examples be read to limit, or to define, the scope of the invention.

EXAMPLES

Example 1: Detection of Ketones at Low Potential Using an Analyte Sensor Having Diaphorase and β-Hydroxybutyrate Dehydrogenase Acting in Concert. For this example, the enzyme system of FIG. 6A was used to facilitate detection of ketones using the active area formulations specified in Tables 1 and 2 below, using either the unbound Formula 8 transition metal complex (Table 1) or the Formula 8 transition metal complex bound to polyvinylpyridine-co-styrene (Table 2) as redox mediators (HBHD=β-hydroxybutyrate dehydrogenase; HSA=human serum albumin; PEGDGE400=polyethylene glycol diglycidyl ether). The sensing active area formulations shown in Tables 1 and 2 were coated onto a carbon coated working electrode by depositing one spot with an area of roughly 0.2 mm². The active area was cured for 24 h at 25° C. Following curing, a polyvinylpyridine membrane having the formulation specified in Table 3 was applied over the active area via dip coating a total of four times. Following application of the membrane, the sensors were cured for 24 h at 25° C. and then for 48 h at 56° C.

TABLE 1

| Component | Final Concentration (mg/mL) in 10 mM MES, pH 5.5 |
|---|---|
| HBDH | 8 |
| Diaphorase | 4 |
| HSA | 8 |
| NAD | 8 |
| Formula 8 Transition Metal Complex | 6.8 |
| PEGDGE400 | 4 |

TABLE 2

| Component | Final Concentration (mg/mL) in 10 mM MES, pH 5.5 |
|---|---|
| HBDH | 8 |
| Diaphorase | 4 |
| HSA | 8 |
| NAD | 8 |
| Polymer-Bound Formula 8 Transition Metal Complex | 8 |
| PEGDGE400 | 4 |

TABLE 3

| Component | Concentration (mg/mL) | Solvent | Volume Added (mL) |
|---|---|---|---|
| PVP | 100 | 80/20 EtOH/HEPES | 4 |
| PDMS | 100 | EtOH | 0.0132 |
| PEGDGE400 | 100 | 80/20 EtOH/HEPES | 0.2 |

Figure 7:
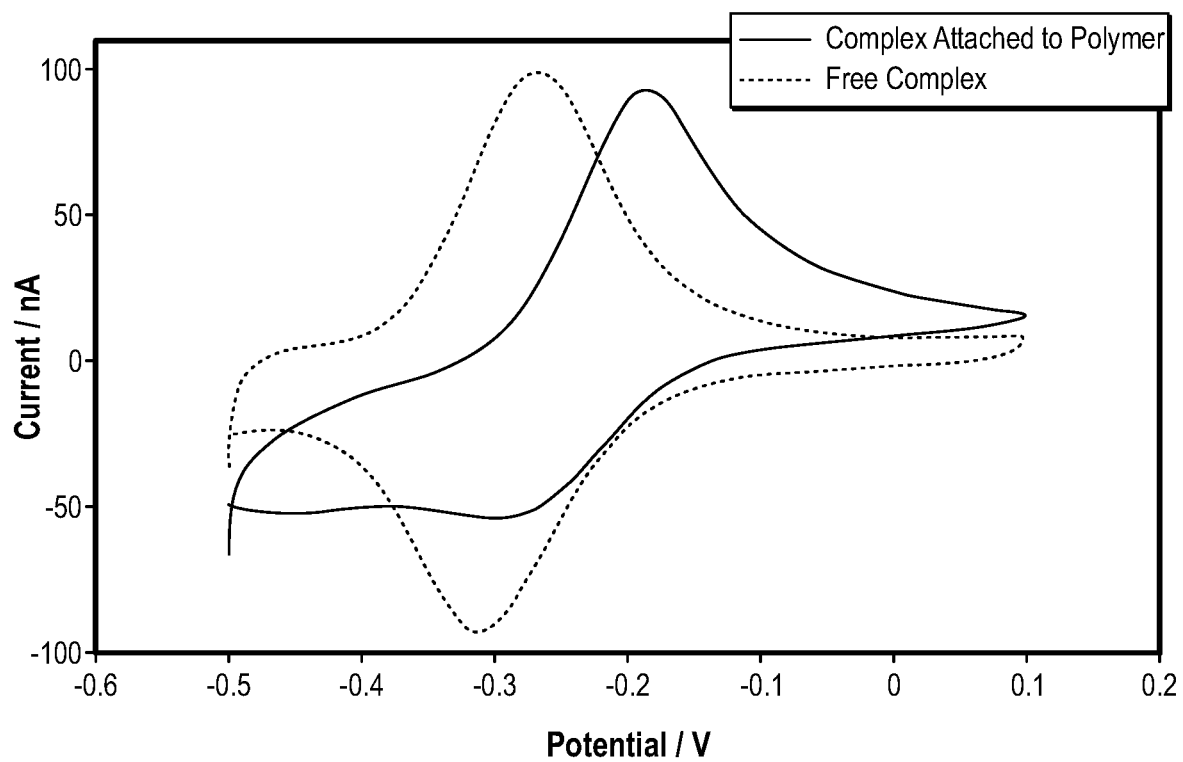
FIG. 7 shows cyclic voltammograms for a low-potential redox mediator in free form and in polymer-bound form.

FIG. 7 shows cyclic voltammograms for the Formula 8 transition metal complex or the polymer-bound Formula 8 transition metal complex. The cyclic voltammograms were obtained in a solution of 100 mM PBS at pH 7.4, which was deoxygenated via nitrogen bubbling and held at a temperature of 33° C. Scanning was conducted from −0.5 V to 0.1 V at a scan rate of 5 mV/s using a carbon counter electrode and a Ag/AgCl reference electrode. From the cyclic voltammograms, the $E_{1/2}$ of the Formula 8 transition metal complex was measured as −0.29 V vs. Ag/AgCl and the $E_{1/2}$ of the polymer-bound Formula 8 transition metal complex was measured as −0.24 V vs. Ag/AgCl. A comparative redox mediator lacking the N,N-dimethylamino substitution exhibited a much less negative $E_{1/2}$ value of −0.08 V vs. Ag/AgCl (data not shown).

Figure 8:
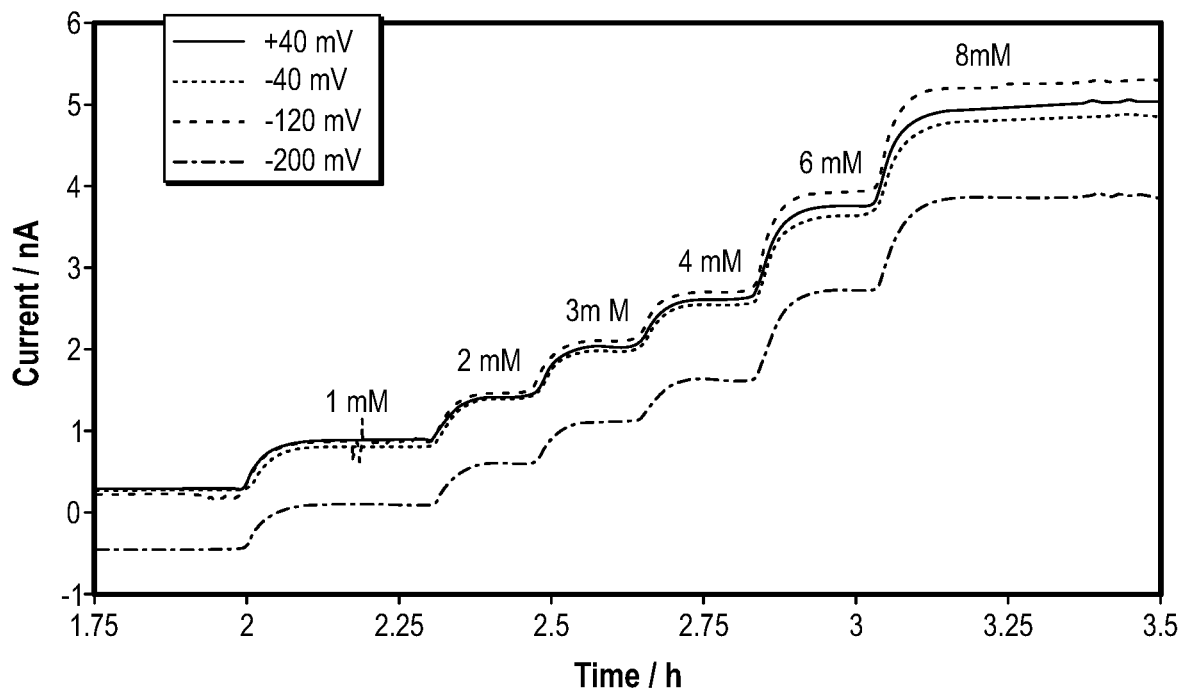
FIG. 8 shows a plot of current versus time at various working electrode potentials for a ketones sensor incorporating a low-potential redox mediator.
Figure 9:
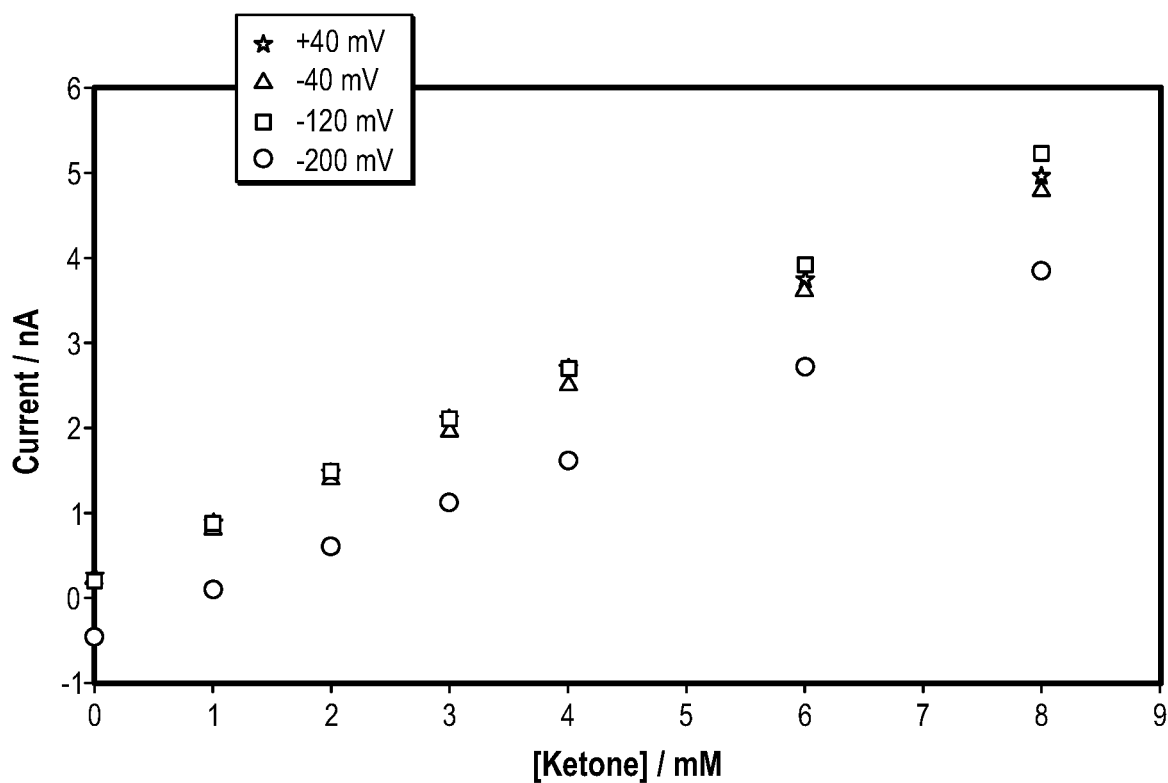
FIG. 9 shows a plot of current versus ketone concentration at various working electrode potentials for a ketones sensor incorporating a low potential redox mediator.

FIG. 8 shows a plot of current versus time for ketone sensors including polymer-bound Formula 8 transition metal complex at various working electrode potentials. The sensors were held at one of four potentials ranging from +40 mV to −200 mV in 100 mM PBS at pH 7.4, and variable amounts of β-hydroxybutyrate were titrated thereto at 33° C. up to a final ketones concentration of 8 mM. As shown, the sensor response rapidly stabilized after adding the ketones at each potential. For each of the four potentials tested, a linear response to the ketone concentration was observed (see FIG. 9).

Example 2: Extractables from a Polyethylene Glycol Tetraglydicyl Ether-Crosslinked Membrane. A polymer membrane sample crosslinked with polyethylene glycol tetraglycidyl ether (molecular weight ~2500) was prepared. The base membrane polymer was a copolymer of vinylpyridine and styrene containing an amine-free polyether arm bound to at least a portion of pyridine moieties in the base membrane polymer. A comparative polymer membrane sample was prepared with the same membrane polymer crosslinked with polyethyelene glycol diglycidyl ether (molecular weight ~1000). The comparative polymer membrane sample was crosslinked with polyethylene glycol diglycidyl ether at a similar mass of crosslinker to that of polyethylene glycol tetraglycidyl ether used in the other sample, thereby providing a similar crosslinking density.

Figure 10:
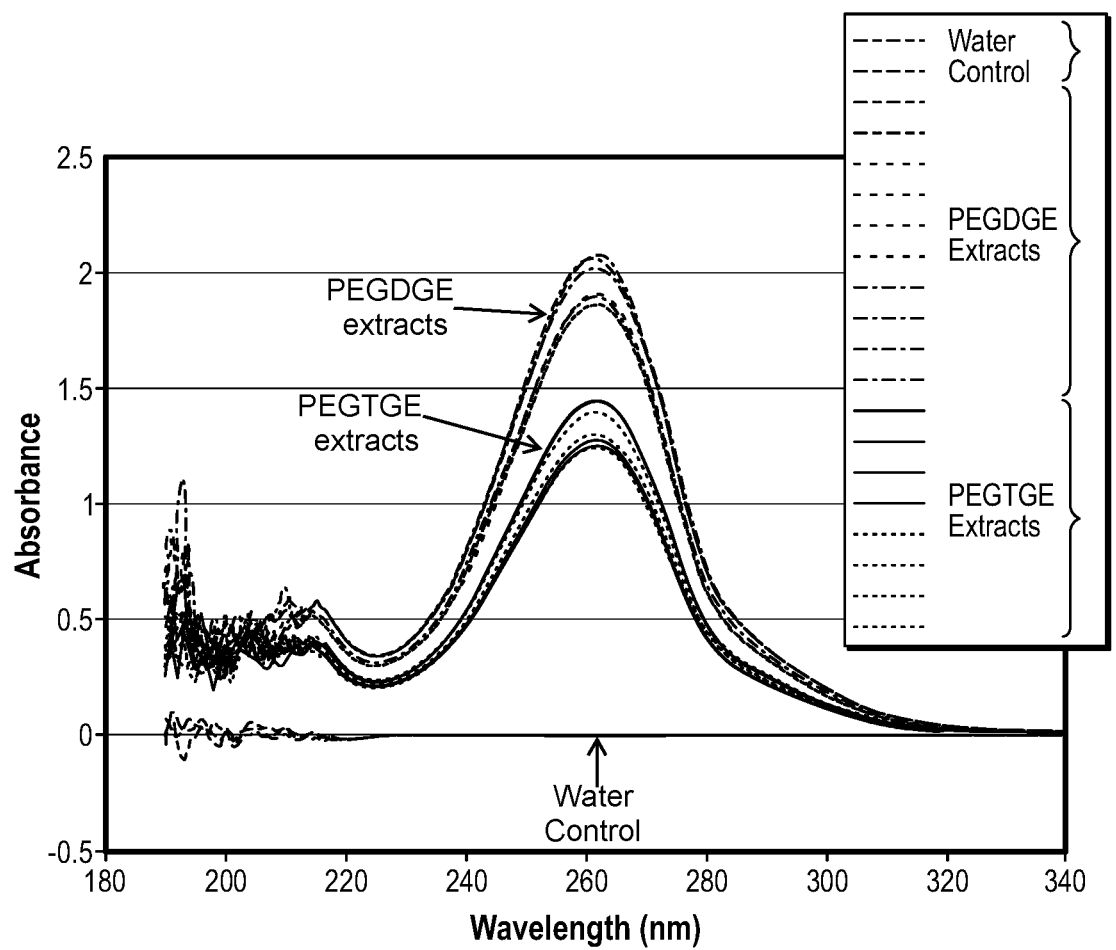
FIGS. 10 and 11 show UV-VIS absorption data for extracts obtained from a membrane polymer crosslinked with polyethylene glycol tetraglycidyl ether in comparison to a membrane polymer crosslinked with polyethylene glycol diglycidyl ether.
Figure 11:
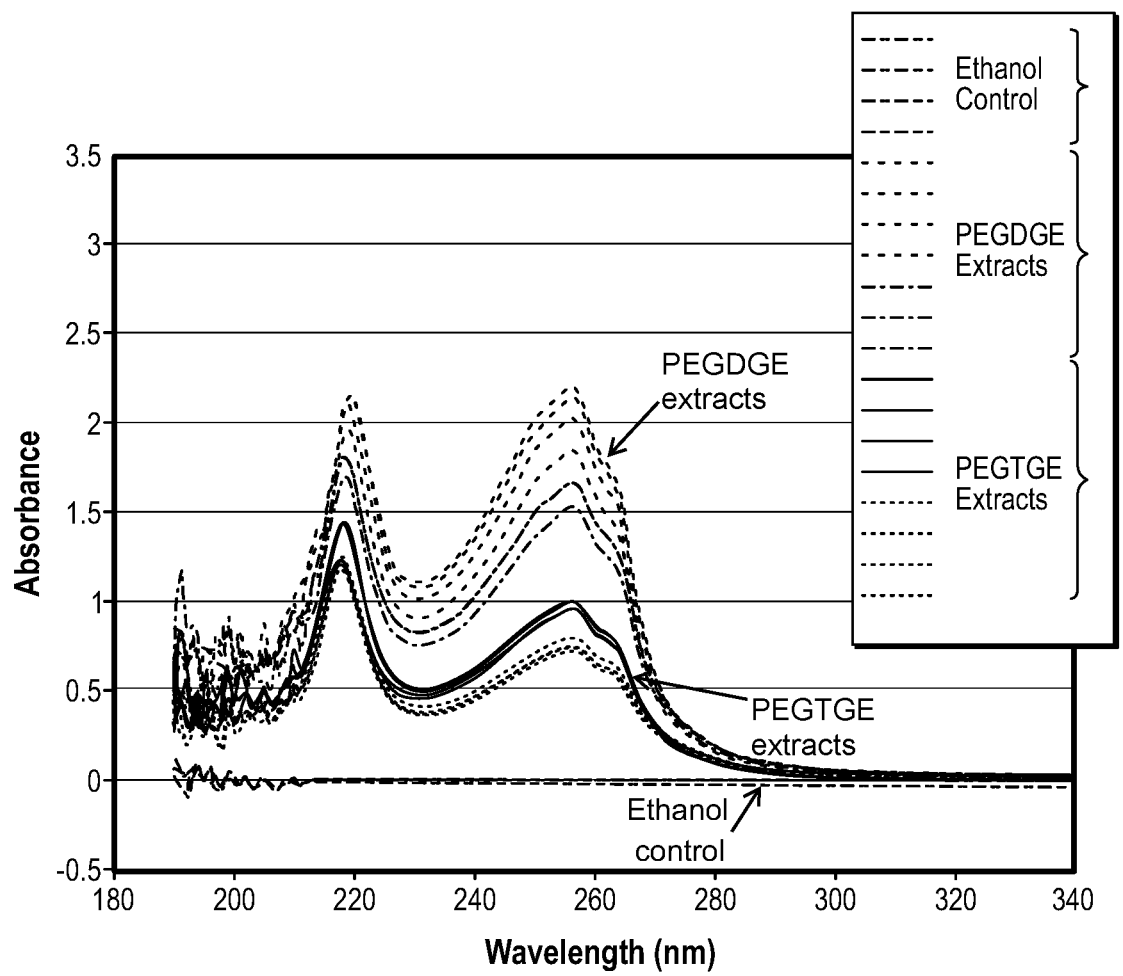

The membrane polymers were cast as films upon the bottom of a sample vial using 0.5 mL of a solution containing the membrane polymer. The solvent was evaporated, and membrane curing then was performed at 25° C. for 48 hours and at 56° C. for 56 hours. Water or 95% ethanol (3 mL) was added to the cast polymer films, and extraction was performed for 72 hours (water) or 144 hours (ethanol) at room temperature. The vial was agitated on a rocker during the extraction period. The water extracts were analyzed neat by UV-Vis spectrophotometry (FIG. 10), and the ethanol extracts were diluted 1:9 before UV-Vis analysis (FIG. 11). As shown by the intensity of the UV-Vis absorbance in both cases, the samples crosslinked with polyethylene glycol tetraglycidyl ether exhibited a lower amount of extractable materials.

Figure 12:
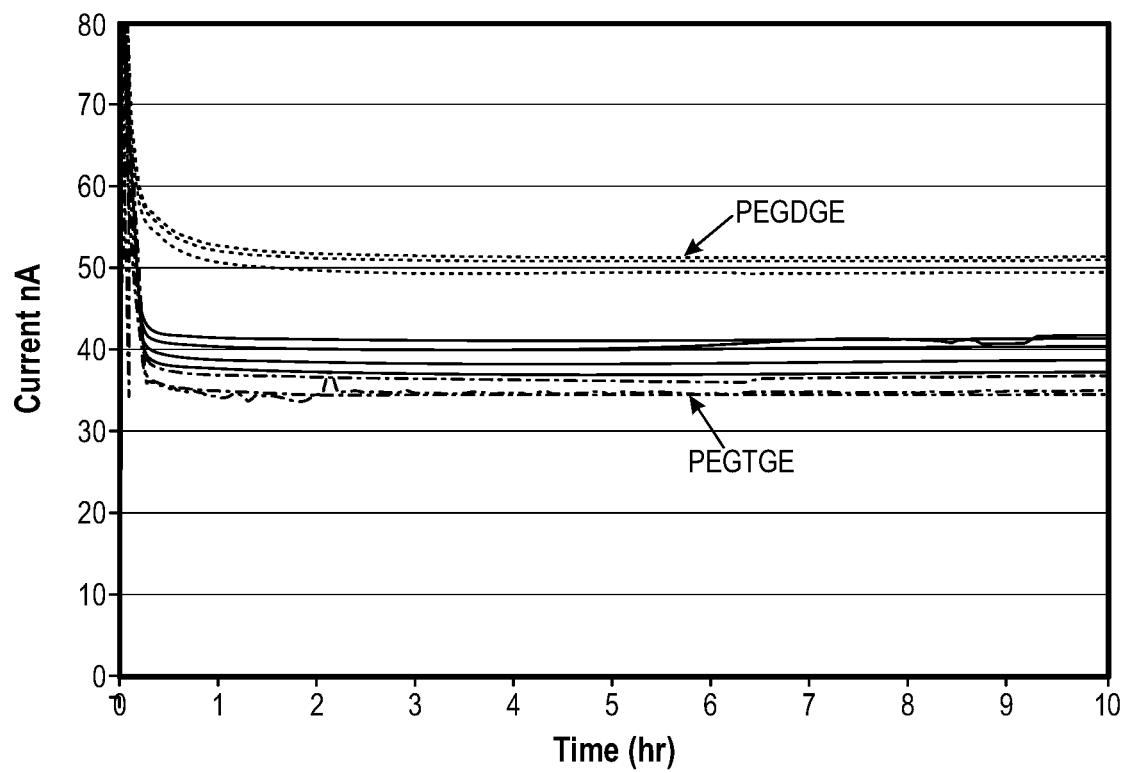
FIGS. 12 and 13 show comparative plots of sensor output versus time for an analyte sensor overcoated with a membrane polymer crosslinked with polyethylene glycol tetraglycidyl ether in comparison to an analyte sensor overcoated with a membrane polymer crosslinked with polyethylene glycol diglycidyl.
Figure 13:
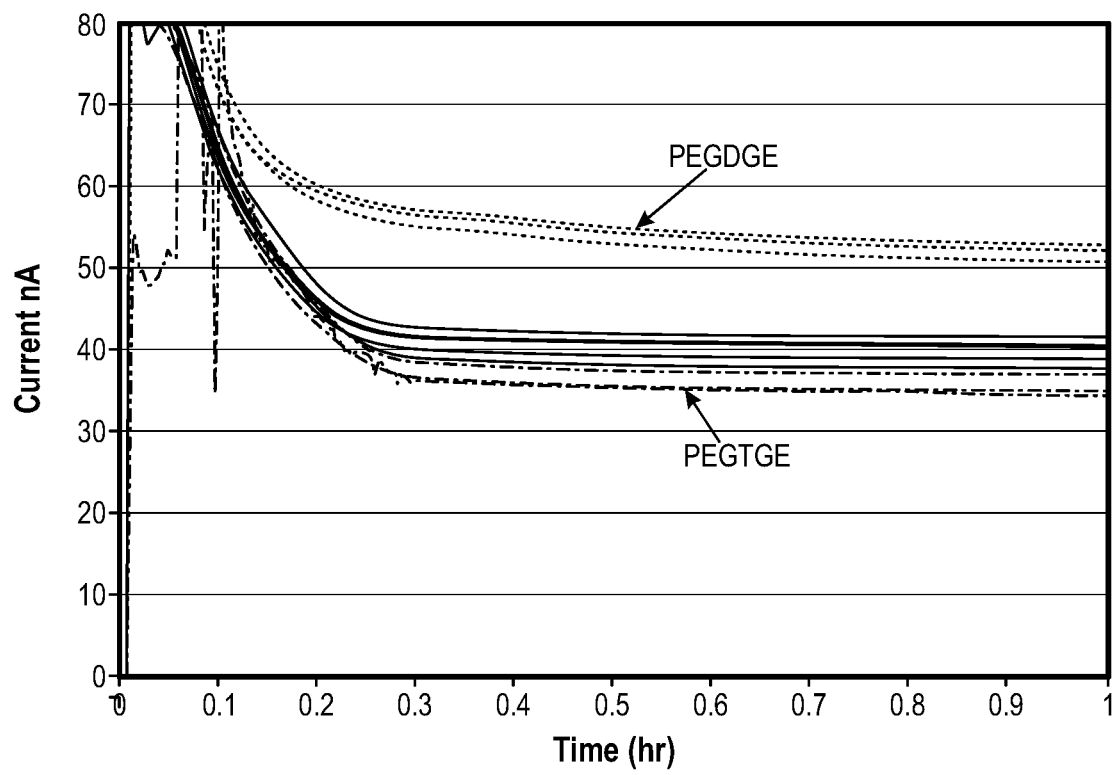

Example 3: Equilibration Time for a Sensor Having a Polyethylene Glycol Tetraglydicyl Ether-Crosslinked Membrane. A glucose-responsive analyte sensor was overcoated with a membrane polymer crosslinked with polyethylene glycol tetraglycidyl ether (see Example 2). A comparative sensor was prepared with a comparable membrane polymer crosslinked with polyethylene glycol diglycidyl ether. Each membrane-coated sensor was placed in a 30 mM glucose solution in 1000 mM PBS (pH=7.4) at 37° C. FIG. 12 shows a comparative plot of sensor output versus time over 10 hours for the analyte sensor overcoated with a polyethylene glycol tetraglycidyl ether-crosslinked membrane polymer in comparison to the analyte sensor overcoated with a polyethylene glycol diglycidyl ether-crosslinked membrane polymer. As shown, both membranes afforded stable sensor outputs after approximately 1 hour of equilibration. FIG. 13 shows an expansion plot of the first hour of sensor equilibration, wherein it can be seen that the polyethylene glycol tetraglycidyl ether-crosslinked membrane afforded a stable response faster than did the polyethylene glycol diglycidyl ether-crosslinked membrane.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the

What is claimed is the following:
1. An analyte sensor comprising:
a sensor tail comprising:
i) a Ag/AgCl reference electrode;
ii) at least a first working electrode and a second working electrode;
iii) a first active area disposed upon a surface of the first working electrode and responsive at low potential to β-hydroxybutyrate, the first active area comprising a first polymer, a first redox mediator covalently bonded to the first polymer, and at least one enzyme responsive to β-hydroxybutyrate covalently bonded to the first polymer;
wherein the low potential is above an oxidation-reduction potential of the first redox mediator and below about −80 mV relative to the Ag/AgCl reference electrode;
wherein the oxidation-reduction potential of the first redox mediator ranges from about −200 mV to about −400 mV relative to the Ag/AgCl reference electrode;
wherein the first redox mediator has a structure of

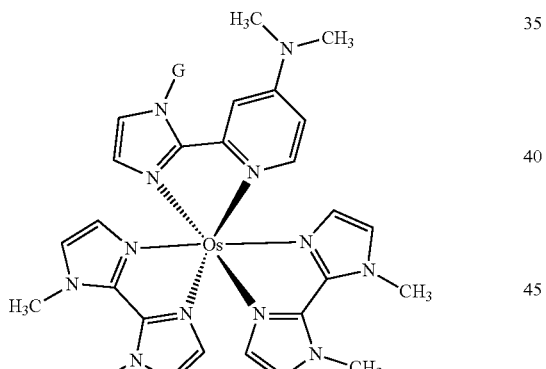

wherein G is a linking group covalently bonding the first redox mediator to the first polymer; and
iv) a second active area disposed upon a surface of the second working electrode and responsive to a second analyte differing from β-hydroxybutyrate, the second active area comprising a second polymer, a second redox mediator differing from the first redox mediator covalently bonded to the second polymer, and at least one enzyme responsive to the second analyte covalently bonded to the second polymer;
wherein the at least one enzyme responsive to the second analyte comprises an enzyme system comprising multiple enzymes that are collectively responsive to the second analyte;
v) a mass transport limiting membrane permeable to 3-hydroxybutyrate that overcoats at least the first active area;
wherein a second portion of the mass transport limiting membrane overcoats the second active area.
2. The analyte sensor of claim 1, wherein the at least one enzyme comprises an enzyme system comprising multiple enzymes that are collectively responsive to β-hydroxybutyrate.
3. The analyte sensor of claim 1, wherein the mass transport limiting membrane comprises a membrane polymer crosslinked with a branched crosslinker comprising three or more crosslinkable groups.
4. The analyte sensor of claim 3, wherein the membrane polymer comprises a polyvinylpyridine or a polyvinylimidazole.
5. The analyte sensor of claim 3, wherein the branched crosslinker comprises polyethyleneglycol tetraglycidyl ether.
6. A method comprising:
exposing an analyte sensor to a fluid comprising β-hydroxybutyrate, the analyte sensor comprising:
a sensor tail comprising:
i) a Ag/AgCl reference electrode;
ii) at least a first working electrode;
iii) a first active area disposed upon a surface of the first working electrode and responsive at low potential to β-hydroxybutyrate, the first active area comprising a first polymer, a first redox mediator covalently bonded to the first polymer, and at least one enzyme responsive to β-hydroxybutyrate covalently bonded to the first polymer;
wherein the at least one enzyme comprises an enzyme system comprising multiple enzymes that are collectively responsive to β-hydroxybutyrate;
wherein the low potential is above an oxidation-reduction potential of the first redox mediator and below about −80 mV relative to the Ag/AgCl reference electrode;
wherein the oxidation-reduction potential of the first redox mediator ranges from about −200 mV to about −400 mV relative to the Ag/AgCl reference electrode;
wherein the first redox mediator has a structure of

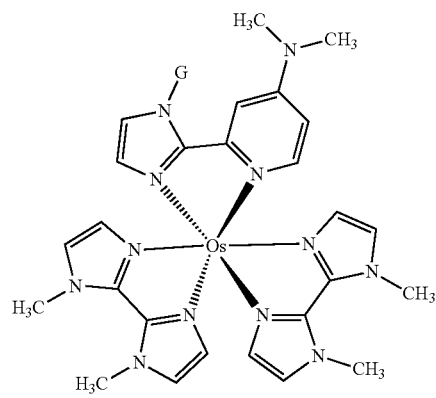

wherein G is a linking group covalently bonding the first redox mediator to the first polymer; and
iv) a mass transport limiting membrane permeable to β-hydroxybutyrate that overcoats at least the first active area;
applying the low potential to the first working electrode;
obtaining a first signal at or above an oxidation-reduction potential of the first active area, the first signal being proportional to a concentration of β-hydroxybutyrate in a fluid contacting the first active area; and
correlating the first signal to the concentration of β-hydroxybutyrate in the fluid.

7. The method of claim 6, wherein the mass transport limiting membrane comprises a membrane polymer crosslinked with a branched crosslinker comprising three or more crosslinkable groups.

8. The method of claim 7, wherein the membrane polymer comprises a polyvinylpyridine or a polyvinylimidazole.

9. The method of claim 7, wherein the branched crosslinker comprises polyethyleneglycol tetraglycidyl ether.

10. The method of claim 6, wherein the analyte sensor further comprises:
a second working electrode; and
a second active area disposed upon a surface of the second working electrode responsive to a second analyte differing from β-hydroxybutyrate, the second active area comprising a second polymer, a second redox mediator differing from the first redox mediator, the second redox mediator covalently bonded to the second polymer, and at least one enzyme responsive to the second analyte covalently bonded to the second polymer;
wherein a second portion of the mass transport limiting membrane overcoats the second active area.

11. The method of claim 10, wherein the at least one enzyme responsive to the second analyte comprises an enzyme system comprising multiple enzymes that are collectively responsive to the second analyte.

12. A method comprising:
exposing an analyte sensor to a fluid comprising β-hydroxybutyrate, the analyte sensor comprising:
a sensor tail comprising:
i) a Ag/AgCl reference electrode; and
ii) at least a first working electrode and a second working electrode;
iii) a first active area disposed upon a surface of the first working electrode and responsive at low potential to β-hydroxybutyrate, the first active area comprising a first polymer, a first redox mediator covalently bonded to the first polymer, and at least one enzyme responsive to β-hydroxybutyrate covalently bonded to the first polymer;
wherein the low potential is above an oxidation-reduction potential of the first redox mediator and below about −80 mV relative to the Ag/AgCl reference electrode;
wherein the oxidation-reduction potential of the first redox mediator ranges from about −200 mV to about −400 mV relative to the Ag/AgCl reference electrode;

wherein the first redox mediator has a structure of

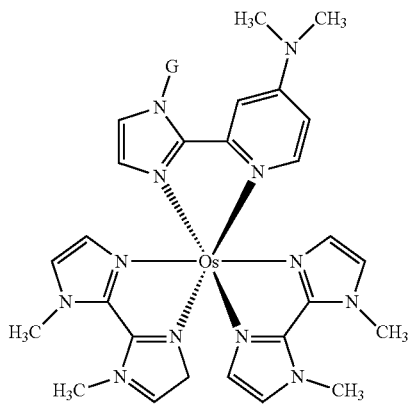

wherein G is a linking group covalently bonding the first redox mediator to the first polymer; and
iv) a second active area disposed upon a surface of the second working electrode and responsive to a second analyte differing from β-hydroxybutyrate, the second active area comprising a second polymer, a second redox mediator differing from the first redox mediator covalently bonded to the second polymer, and at least one enzyme responsive to the second analyte covalently bonded to the second polymer;
wherein the at least one enzyme responsive to the second analyte comprises an enzyme system comprising multiple enzymes that are collectively responsive to the second analyte
v) a mass transport limiting membrane permeable to β-hydroxybutyrate that overcoats at least the first active area;
wherein a second portion of the mass transport limiting membrane overcoats the second active area;
applying the low potential to the first working electrode;
obtaining a first signal at or above an oxidation-reduction potential of the first active area, the first signal being proportional to a concentration of β-hydroxybutyrate in a fluid contacting the first active area; and
correlating the first signal to the concentration of β-hydroxybutyrate in the fluid.

* * * * *